United States Patent
Chen et al.

(10) Patent No.: US 10,792,274 B2
(45) Date of Patent: Oct. 6, 2020

(54) DEHYDROACETIC ACID (DHAA) AND DERIVATIVE FOR USES IN TREATING CANCER

(71) Applicants: Emory University, Atlanta, GA (US); The United States Government as Represented by the Department of Veterans Affairs, Washington, DC (US)

(72) Inventors: Jing Chen, Atlanta, GA (US); Jack Arbiser, Atlanta, GA (US); Brian Pollack, Decatur, GA (US); Siyuan Xia, Atlanta, GA (US)

(73) Assignees: Emory University, Atlanta, GA (US); The United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/386,763

(22) Filed: Apr. 17, 2019

(65) Prior Publication Data
US 2020/0000764 A1  Jan. 2, 2020

Related U.S. Application Data

(62) Division of application No. 15/804,299, filed on Nov. 6, 2017, now abandoned.

(60) Provisional application No. 62/417,928, filed on Nov. 4, 2016.

(51) Int. Cl.
*A61K 31/351* (2006.01)

(52) U.S. Cl.
CPC .................. *A61K 31/351* (2013.01)

(58) Field of Classification Search
CPC .................................................. A61K 31/351
See application file for complete search history.

(56) References Cited

U.S. PATENT DOCUMENTS

| | | | |
|---|---|---|---|
| 7,994,185 B2 | 8/2011 | Rheault | |
| 9,211,275 B2 | 12/2015 | Clarke | |
| 2006/0009506 A1 | 1/2006 | Westwick | |
| 2008/0275016 A1 | 11/2008 | Arbiser | |
| 2018/0125812 A1* | 5/2018 | Chen .................... | A61K 31/351 |

FOREIGN PATENT DOCUMENTS

WO  2016065353  4/2016

OTHER PUBLICATIONS

Bi et al. Triparanol suppresses human tumor growth in vitro and in vivo, Biochemical and Biophysical Research Communications 425 (2012) 613-618.
Bocci et al. Fluvastatin synergistically enhances the antiproliferative effect of gemcitabine in human pancreatic cancer MIAPaCa-2 cells, British Journal of Cancer (2005) 93, 319-330.
Chan et al. Dietary fat and growth promotion of rat mammary tumors. Cancer Res. 1975, 35:3384.
Chen et al. High fat diet increases melanoma cell growth in the bone marrow by inducing osteopontin and interleukin 6, Oncotarget, 2016, 7(18): 26653-26669.
Davies et al. Mutations of the BRAF gene in human cancer, Nature, 2002, 417, 949-954.
Elf et al. Targeting Glucose Metabolism in Patients With Cancer, Cancer. 2014, 120(6): 774-780.
Firestone, Low-Density Lipoprotein as a Vehicle for Targeting Antitumor Compounds to Cancer Cells, Bioconjugate Chem. 1994, 5, 105-113.
Garwood et al. Fluvastatin reduces proliferation and increases apoptosis in women with high grade breast cancer, Breast Cancer Res Treat. 2010, 119(1): 137-144.
Grabacka et al. Inhibition of melanoma metastases by fenofibrate, Arch Dermatol Res (2004) 296 : 54-58.
Gynn et al. The 3-hydroxy-3-methylglutaryl-coenzyme a reductase inhibitors, simvastatin, lovastatin and mevastatin inhibit proliferation and invasion of melanoma cells, BMC Cancer 2008, 8:9.
Hindler et al. The Role of Statins in Cancer Therapy, The Oncologist, 2006,11:306-315.
Kang et al. Metabolic Rewiring by Oncogenic BRAF V600E Links Ketogenesis Pathway to BRAF-MEK1 Signaling, 2015, Molecular Cell 59, 345-358.
Kirsner et al. Lipid-lowering agents and risk of melanoma, Int. J. Cancer: 117, 333 (2005).
Lin et al. 6-phosphogluconate dehydrogenase links oxidative PPP, lipogenesis and tumor growth by inhibiting LKB1-AMPK signaling, Nat Cell Biol. 2015, 17(11): 1484-1496.
Malvi et al. Obesity induced rapid melanoma progression is reversed by orlistat treatment and dietary intervention: Role of adipokines, Mol Onoc, 2015, 9, 689.
Miyaki et al. Inhibitory Effect of Dehydroacetic Acid on Induction of Hepatoma in Rats Fed 4-(Dimethylamino) Azobenzene, Gann, 59, 85-95, 1968.
Orime et al. Lipid-lowering agents inhibit hepatic steatosis in a non-alcoholic steatohepatitis-derived hepatocellular carcinoma mouse model, European J Pharma, 2016, 772, 22-32.
Sato et al. Effect of Pravastatin on Plasma Ketone Bodies in Diabetics with Hypercholesterolemia, Tohoku J Exper Med, 1998, 185, 25-29.
Styers, Triacylglycerols are hydrolyzed by cyclic amp regulated lipases, Chapter 17 Fatty Acid Metabolism, 1981, 386-393.
Tang et al. Insight into molecular dynamics simulation of BRAF(V600E) and potent novel inhibitors for malignant melanoma, International Journal of Nanomedicine 2015, 10 3131-3146.

(Continued)

*Primary Examiner* — Rei Tsang Shiao
(74) *Attorney, Agent, or Firm* — Emory Patent Group

(57) ABSTRACT

This disclosure relates to methods of managing or treating cancer with agents that lower circulating acetoacetate levels, such as hypolipidemic agents, or other agents that antagonize acetoacetate-BRAF V600 mutant binding to attenuate BRAF V600 mutant tumor growth. In certain embodiments, this disclosure relates to methods of treating cancer comprising administering an effective amount of an agent to a subject in need thereof, wherein the agent is dehydroacetic acid, derivative, prodrug, or salt thereof.

4 Claims, 28 Drawing Sheets

(56) References Cited

OTHER PUBLICATIONS

Xia et al. Prevention of dietary fat-fueled ketogenesis attenuates BRAF V600E tumor growth, Cell Metab. 2017, 25(2): 358-373.
Zhang et al. Fluvastatin Enhances Sorafenib Cytotoxicity in Melanoma Cells via Modulation of AKT and JNK Signaling Pathways, Anticancer Research 31: 3259-3266 (2011).

* cited by examiner

| BRAF  | Kd (µM)       |
|-------|---------------|
| WT    | NR            |
| V600E | 91.99 ± 21.30 |
| V600D | 92.74 ± 24.84 |
| V600R | 112.6 ± 25.04 |
| V600A | NR            |
| L597Q | NR            |
| K601E | NR            |

| BRAF  | Ki (µM)      |
|-------|--------------|
| WT    | NR           |
| V600E | 87.54 ± 1.29 |
| V600D | 88.37 ± 1.27 |
| V600R | 90.70 ± 1.29 |
| V600A | NR           |
| L597Q | NR           |
| K601E | NR           |

DEHYDROACETIC ACID (DHAA) AND DERIVATIVE FOR USES IN TREATING CANCER

CROSS-REFERENCE TO RELATED APPLICATIONS

This application is a division of U.S. application Ser. No. 15/804,299 filed Nov. 6, 2017, which claims the benefit of U.S. Provisional Patent Application No. 62/417,928 filed Nov. 4, 2016. The entirety of each of these applications is hereby incorporated by reference for all purposes.

STATEMENT REGARDING FEDERALLY FUNDED RESEARCH

This invention was made with government support under CA140515 awarded by the National Institutes of Health. The government has certain rights in the invention.

BACKGROUND

Mutations in various Ras GTPases and the B-Raf kinase have been identified that can lead to sustained and constitutive activation of the MAPK pathway, ultimately resulting in increased cell division and survival. As a consequence of this, these mutations have been strongly linked with the establishment, development, and progression of a wide range of human cancers. Naturally occurring mutations of the B-Raf kinase that activate MAPK pathway signaling have been found in a large percentage of human melanomas and other cancers (See e.g., Davies, H., et al., Nature (2002) 9:1-6).

Kang et al. report metabolic rewiring by oncogenic BRAF V600E links ketogenesis pathway to BRAF-MEK1 signaling. Molecular Cell, 2015, 59, 345-358. 3-Hydroxy-3-methylglutaryl-CoA lyase (HMGCL) expression is upregulated in BRAF V600E-expressing human primary melanoma and hairy cell leukemia cells, and suppression of HMGCL specifically attenuates proliferation and tumor growth potential of human melanoma cells expressing BRAF V600E.

Arbiser et al. report fulvene and fulvalene analogs and there use in treating cancer. See US 20080275016.

Miykai et al. report an inhibitory effect of dehydroacetic acid on induction of hepatomas in rats feed 4-(methylamino) azobenzene. GANN Japanese Journal of Cancer Research, Vol. 59 (1968) No. 2 P 85-96. Dehydroacetic acid (CAS No. 520-45-6) and dehydroacetic acid sodium salt (CAS No. 4418-26-2) are used as stabilizers for cosmetic and pharmaceutical products.

Rheault report benzene sulfonamide thiazole and oxazole compounds for use in the treatment of a condition mediated by at least one Raf family kinases (e.g., B-Raf). See U.S. Pat. No. 7,994,185.

References cited herein are not an admission of prior art.

SUMMARY

This disclosure relates to methods of managing or treating cancer with agents that lower circulating acetoacetate levels, such as hypolipidemic agents, or other agents that antagonize acetoacetate-BRAF V600 mutant binding to attenuate BRAF V600 mutant tumor growth. In certain embodiments, this disclosure relates to methods of treating cancer comprising administering an effective amount of an agent to a subject in need thereof, wherein the agent is dehydroacetic acid, derivative, prodrug, or salt thereof.

In certain embodiments, the agent that lower circulating acetoacetate levels is a hypolipidemic agent. In certain embodiments, the hypolipidemic agent is selected from a statin, fibrate, niacin, bile acid sequestrant, ezetimibe, lomitapide, phytosterol, orlistat, CEPT inhibitor, squalene synthase inhibitor, ApoA-1 Milano, succinobucol, mipomersen, PCSK9 monoclonal antibody inhibitors.

In certain embodiments, this disclosure relates to methods of treating cancer comprising administering an effective amount of an agent that antagonizes acetoacetate-BRAF V600 mutant binding, e.g. V600E, V600D and V600R mutants, to attenuate BRAF V600 mutant tumor growth to a subject in need thereof.

In certain embodiments, this disclosure relates to combination therapies using compounds disclosed herein such as hypolipidemic agents or dehydroacetic acid, derivatives, prodrugs, or salts, in combination with one or more chemotherapy agents.

In certain embodiments, the disclosure relates to pharmaceutical products comprising compounds disclosed herein such as hypolipidemic agents or dehydroacetic acid, derivatives, prodrugs, or salts, and one or more chemotherapy agents.

In certain embodiments, the disclosure relates to methods of effectively treating subject with cancer comprising limiting dietary fat intake and optionally administering compounds disclosed herein and optionally in combination with another chemotherapeutic agent. In certain embodiments, the method further comprises measuring circulating acetoacetate levels in a blood sample from the subject. In certain embodiments, the acetoacetate levels are compared to a threshold value and wherein if acetoacetate levels are above the threshold value, then dietary fat intake is decreased.

In certain embodiments, the subject is diagnosed with a mutation encoding at V600 amino acid substitution present in the coding sequence for B-Raf.

In certain embodiments, the subject is diagnosed with metastatic melanoma.

In certain embodiments, the subject is diagnosed with a BRAF V600E-positive malignant or premalignant lesions.

DETAILED DISCUSSION

Figure 1A:
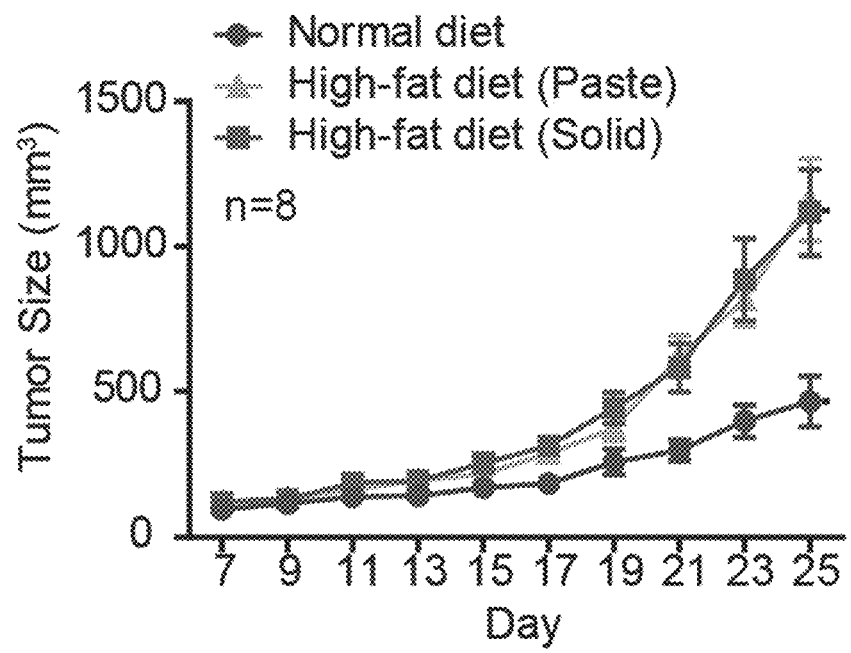
FIG. 1A shows data indicating a high-fat diet selectively promotes tumor growth potential of BRAF V600E positive melanoma cells in xenograft nude mice. Xenograft tumor growth of nude mice inoculated with human melanoma BRAF V600E-positive A375, fed with normal diet, or different high-fat diets.
Figure 1B:
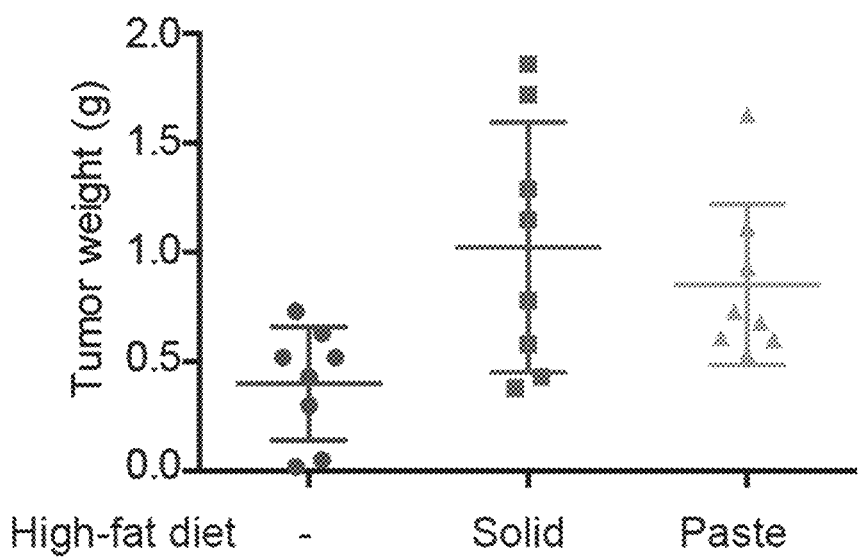
FIG. 1B shows data for tumor weight.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Certain of the compounds described herein may contain one or more asymmetric centers and may give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, tautomer forms, hydrated forms, optically substantially pure forms and intermediate mixtures.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine, and chlorine, such as, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Certain isotopically-labeled disclosed compounds (e.g., those labeled with $^{3}H$ and/or $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

As used herein, "alkyl" means a noncyclic straight chain or branched, unsaturated or saturated hydrocarbon such as those containing from 1 to 22 carbon atoms, while the term "lower alkyl" or "$C_{1-4}$ alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The term "halogenated alkyl" refers to an alkyl substituted with one or more halogens, e.g., trifluoromethyl.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or eterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic. "Arylalkyl" means an alkyl substituted with an aryl, e.g., benzyl, methyl substituted with phenyl.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, and t-butoxy.

"Alkylamino" refers to an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

"Aminoalkyl" refers to an amino group attached through an alkyl bridge. An example of an aminoalkyl is aminomethyl, (i.e., $NH_2$—$CH_2$—).

"Hydroxyalkyl" refers to a hydroxy group attached through an alkyl bridge. An example of a hydroxyalkyl is hydroxyethyl, (i.e., HO—$CH_2CH_2$—).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carb ocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral salts such as sodium, potassium, or zinc carboxylic acid salts, or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers to any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry:

Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, idoxifene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); adriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Dehydroacetic Acid and Derivatives Useful for BRAF-V600E Positive Cancer Treatment It has been discovered that a high-fat ketogenic diet increased serum levels of acetoacetate leading to enhanced tumor growth potential of BRAF V600E-expressing human melanoma cells. Ketogenesis mainly occurs in the mitochondria of liver cells, which normally produces ketone bodies as a result of fatty acid breakdown to generate energy when glucose levels in the blood are low. HMGCL converts HMG-CoA to acetyl-coA and a ketone body, acetoacetate (AA), which can be further converted to two other ketone bodies, including D-β-hydroxybutyrate (3-HB) and acetone. It was discovered that active BRAF upregulates HMGCL via an octamer transcription factor Oct-1. Consistently, BRAF V600E expression results in increased HMGCL gene expression in cancer cells. HMGCL, however, selectively promotes BRAF V600E dependent phosphorylation and activation of MEK1 by controlling intracellular levels of its product acetoacetate, which specifically promotes BRAF V600E (but not BRAF WT) binding to MEK1. These results support an emerging "metabolic rewiring" concept in which distinct oncogenes may require different metabolic alterations for tumor growth.

These findings indicate that a ketogenic diet would likely worsen the disease burden in BRAF V600E-positive cancer patients. Acetoacetate is cell permeable. In addition to the increased intracellular acetoacetate levels induced by BRAF V600E, a hypothesis that dietary fat-fueled ketogenesis may promote BRAF V600E melanoma growth in vivo through increased serum concentrations of acetoacetate was tested. Experimental findings indicate a pathogenic connection between a dietary component and a particular oncogenic mutation in human cancer.

Particular oncogenic mutations (such as BRAF V600E) may require specific metabolic alterations for cancer development, which could be "fueled" by certain dietary components (such as dietary fat).

Although it is not intended that certain embodiments of the disclosure be limited by any particular mechanism, experimental results indicate molecular mechanisms underlying the selective effect of dietary fat on tumor growth potential of BRAF V600E-expressing melanoma cells in vivo, which is mediated through elevated ketogenesis and consequently increased circulating levels of acetoacetate. Most importantly, these studies provide new insights into the development of a new concept that we have named the "precision diet." Such personalized diet should be specifically designed based on an individual's particular mutational background and aims to reduce cancer risk or progression by both depleting dietary components that fuel tumor growth, and providing dietary supplements that prevent cancer development.

In certain embodiments, this disclosure relates to methods of limiting dietary fat intake and monitoring circulating acetoacetate levels might be beneficial in patients with cancer or melanoma having a BRAF V600E or other mutation, and in individuals with BRAF V600E-positive premalignant lesions.

In certain embodiments, the disclosure relates to using lipid lowering agents in cancer prevention and/or supplemental treatment approaches to reduce cancer progression and/or improve clinical outcome in both the BRAF V600E-positive premalignancy and cancer settings.

Dehydroacetic Acid and Derivatives

Figure 4A:
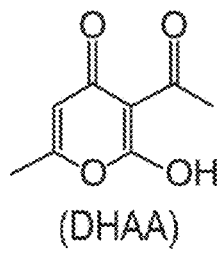
FIG. 4A illustrated the chemical structure formula of dehydroacetic acid (DHAA).

In certain embodiments, a compound disclosed herein is dehydroacetic acid (DHAA), derivatives, prodrugs, and salts thereof. DHAA is termed 3-Acetyl-2-hydroxy-6-methyl-4H- pyran-4-one using IUPAC nomenclature and the formula is depicted in FIG. 4A. In certain embodiments, dehydroacetic acid and derivatives have of the following formula:

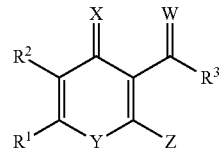

prodrugs or salts thereof wherein,
X is O, S, or NH;
X is O, S, or NH;
Y is O, S, or NH;
Z is OH, SH, or $NH_2$ optionally substituted with one or more, the same or different, $R^{10}$;
$R^1$ is hydrogen, halogen, alkyl, halogenated alkyl, formyl, carboxy, hydroxyalkyl, thioalkyl, aminoalkyl, alkanoyl, alkoxycarbonyl, alkylsulfinyl, alkyl sulfonyl, aryl sulfonyl, carbocyclyl, benozyl, benzyl, aryl, or heterocyclyl, wherein $R^1$ is optionally substituted with one or more, the same or different, $R^{10}$;
$R^2$ is hydrogen, halogen, alkyl, halogenated alkyl, formyl, carboxy, hydroxyalkyl, thioalkyl, aminoalkyl, alkanoyl, alkoxycarbonyl, alkylsulfinyl, alkyl sulfonyl, aryl sulfonyl, carbocyclyl, benozyl, benzyl, aryl, or heterocyclyl, wherein $R^2$ is optionally substituted with one or more, the same or different, $R^{10}$;
$R^3$ is hydrogen, alkyl, halogenated alkyl, formyl, carboxy, hydroxyalkyl, thioalkyl, aminoalkyl, alkanoyl, alkoxycarbonyl, alkylsulfinyl, alkyl sulfonyl, aryl sulfonyl, carbocyclyl, benozyl, benzyl, aryl, or heterocyclyl, wherein $R^3$ is optionally substituted with one or more, the same or different, $R^{10}$; and
$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benozyl, benzyl, aryl, or heterocyclyl, wherein $R^{10}$ is optionally substituted with one or more, the same or different, $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydroxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benozyl, benzyl, carbocyclyl, aryl, or heterocyclyl.

In certain embodiments, $R^1$ is alkyl. In certain embodiments, $R^2$ is hydrogen. In certain embodiments, $R^3$ is alkyl. In certain embodiments, W is O. In certain embodiments, X is O. In certain embodiments, Y is O. In certain embodiments, Z is O. In certain embodiment, $R^1$, $R^2$, and/or $R^3$ are trifluoromethyl.

Methods of Use

This disclosure relates to methods of managing cancer. In certain embodiments, this disclosure relates to methods of treating cancer comprising administering an effective amount of an agent to a subject in need thereof, wherein the agent lowers circulating acetoacetate levels, such as a dehydroacetic acid, derivative, or salt thereof.

In certain embodiments, the agent that lower circulating acetoacetate levels is a hypolipidemic agent. In certain embodiments, the hypolipidemic agent is selected from a statin, fibrate, niacin, bile acid sequestrant, ezetimibe, lomitapide, phytosterol, orlistat, CEPT inhibitor, anacetrapib, squalene synthase inhibitor, ApoA-1 Milano, succinobucol, Mipomersen, PCSK9 monoclonal antibody inhibitors, alirocumab, and evolocumab.

In certain embodiments, the statin (HMG-CoA reductase inhibitor) is selected from atorvastatin, fluvastatin, lovastatin, pitavastatin, pravastatin, rosuvastatin and simvastatin.

In certain embodiments, the fibrate is selected from bezafibrate, ciprofibrate, clofibrate, gemfibrozil, fenofibrate, and clinofibrate.

In certain embodiments, the bile acid sequestrant is cholestyramine, colestipol, or colesevelam.

In certain embodiments, the phytosterol is selected from β-sitosterol, campesterol, cholesterol, stigmasterol, stigmastanol, campestanol, brassicasterol, ergosterol, lupeol, and cycloartenol.

In certain embodiments, this disclosure relates to methods of treating cancer comprising administering an effective amount of dehydroacetic acid, derivative, or salt thereof to a subject in need thereof. In certain embodiments, the subject is suffering from a neoplasm. In certain embodiments, the neoplasm has a mutation encoding a V600E amino acid substitution present in the coding sequence for B-Raf or other mutation. In certain embodiments, the subject is suffering from metastatic melanoma.

In certain embodiments, dehydroacetic acid, derivative, or salt thereof is administered in combination with a second therapeutic agent. In certain embodiments, the second therapeutic agent is a BRAF inhibitor selected from vemurafenib and dabrafenib. In certain embodiments, the second therapeutic agent is a MEK inhibitor selected from trametinib and cobimetinib. In certain embodiments, the second therapeutic agent is imatinib or nilotinib.

Accordingly, compounds of this disclosure may be used in the treatment of a neoplasm, particularly a susceptible neoplasm (a cancer or tumor) in a mammal. The present disclosure also provides a method for treating a neoplasm, particularly a susceptible neoplasm in a mammal in need thereof, which method comprises administering to the mammal a therapeutically effective amount of the compound disclosed herein. In certain embodiments, the disclosure also provides the use of a compound disclosed herein for the preparation of a medicament for the treatment of neoplasm, particularly a susceptible neoplasm, in a mammal.

In certain embodiment, this disclosure relates to methods for the treatment a subject at risk of, exhibiting symptoms of, suspected of, or diagnosed with a cancer or neoplasm selected from skin cancer, melanoma, Barret's adenocarcinoma; biliary tract carcinomas; breast cancer; cervical cancer; cholangiocarcinoma; central nervous system tumors including primary CNS tumors such as glioblastomas, astrocytomas (including glioblastoma multiforme) and ependymomas, and secondary CNS tumors (i.e., metastases to the central nervous system of tumors originating outside of the central nervous system), colorectal cancer, including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; and thyroid cancers.

In certain embodiments, this disclosure relates to the use of a compound disclosed herein for the preparation of a medicament for the treatment of Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers, or any subset thereof, in a mammal (e.g., human).

The compounds disclosed herein can be used alone in the treatment of each of the foregoing conditions or can be used to provide additive or potentially synergistic effects with certain existing chemotherapies, radiation, biological or immunotherapeutics (including monoclonal antibodies) and vaccines. The compounds disclosed herein may be useful for restoring effectiveness of certain existing chemotherapies and radiation and or increasing sensitivity to certain existing chemotherapies and/or radiation.

In certain embodiments, this disclosure provides a method for treating a susceptible neoplasm in a mammal in need thereof comprising the steps of: (a) analyzing a sample from said neoplasm to determine whether an activating mutation is present in the coding sequence for B-Raf in cells of said neoplasm; (b) selecting a mammal having a neoplasm with an activating mutation in the coding sequence for B-Raf; and (c) administering a therapeutically effective amount of a compound disclosed herein to the mammal selected in step (b).

In certain embodiments, the activating mutation present in the coding sequence for BRAF results in a BRAF having an amino acid substitution selected from the group consisting of R462I, I463S, G464V, G464E, G466A, G466E, G466V, G469A, G469E, D594V, F595L, G596R, L597V, L597R, T5991, V600E, V600D, V600K, V600R, T119S, and K601E. See, for example, FIG. 2 of Halilovic and Solvit (2008) Current Opinion in Pharmacology 8:419-26.

In certain embodiments, this disclosure relates to a method for treating a susceptible neoplasm in a mammal in need thereof comprising the steps of: (a) analyzing a sample from said neoplasm to determine whether a mutation encoding a V600E, V600D or V600R amino acid substitution is present in the coding sequence for B-Raf in cells of said neoplasm; (b) selecting a mammal having a neoplasm with a mutation encoding the V600E, V600D or V600R amino acid substitution in B-Raf; and (c) administering a therapeutically effective amount of a compound disclosed herein to the mammal selected in step (b).

The V600E amino acid substitution in B-Raf is described, for example, in Kumar et al. (2004) J Invest Dermatol. 122(2):342-8. This mutation commonly results from a T1799A mutation in the coding sequence for human B-Raf. Accordingly, in one embodiment of the present disclosure, the step of analyzing a sample from said neoplasm to determine whether a mutation encoding a V600E amino acid substitution is present in the coding sequence for B-Raf is performed by determining whether the coding sequence for B-Raf in cells of the neoplasm contains the T1799A mutation.

In one preferred embodiment, the neoplasm is melanoma.

In particular embodiments, the neoplasm is selected from breast cancer, cholangiocarcinoma, colorectal cancer, melanoma, non-small cell lung cancer, ovarian cancer, and thyroid cancer.

In certain embodiments, the mammal is a human.

The sample of the neoplasm to be analyzed for the presence of B-raf activating mutations can be derived from a variety of sources including, but not limited to, single cells, a collection of cells, tissue, cell culture, bone marrow, blood, or other bodily fluids. The tissue or cell source may include a tissue biopsy sample, a cell sorted population, cell culture, or a single cell. In selecting a sample, the percentage of the sample that constitutes neoplastic cells should be considered. In some embodiments, the sample from the neoplasm is fixed using a preservative prior to analyzing for the presence of an activating mutation.

The step of analyzing a sample from the neoplasm to determine whether an activating mutation is present in the coding sequence for B-Raf in cells of said neoplasm may be performed using any method known in the art. For example, the coding sequence for B-raf in cells of the sample may be analyzed to determine if it contains a mutation which results in the expression of activated B-Raf. Methods for detecting such mutations are well known in the art. See, for example, Whitcombe et al. (1999) Nature Biotechnology 17:804-7, Gibson (2006) Clinica Chimica Acta 363: 32-47, Kim and Misra (2007) Annual Review of Biomedical Engineering 9:289-320, and U.S. Pat. Nos. 6,326,145 and 6,270,967). Alternatively, activating mutations in B-Raf may be identified by directly detecting the activated B-raf protein using an agent (e.g. an antibody) that selectively binds activated B-raf.

The precise therapeutically effective amount of the compounds of this disclosure will depend on a number of factors. There are variables inherent to the compounds including, but not limited to, the following: molecular weight, absorption, bioavailability, distribution in the body, tissue penetration, half-life, metabolism, protein binding, and excretion. These variables determine what dose of compound needs to be administered in a sufficient percentage and for a sufficient amount of time to have the desired effect on the condition being treated (e.g., neoplasm). The duration of drug exposure will be limited only by the compound half-life, and side effects from treatment requiring cessation of dosing. The amount of compound administered will also depend on factors related to patients and disease including, but not limited to, the following: the age, weight, concomitant medications and medical condition of the subject being treated, the precise condition requiring treatment and its severity, the nature of the formulation, and the route of administration. Ultimately the dose will be at the discretion of the attendant physician or veterinarian. Typically, the compound disclosed herein will be given for treatment in the range of 0.01 to 30 mg/kg body weight of recipient (mammal) per day or per dose or per cycle of treatment and more usually in the range of 0.1 to 10 mg/kg body weight per day or per dose or per cycle of treatment. Thus, for an adult human being treated for a condition, the actual amount per day or per dose or per cycle of treatment would usually be from 1 to 2000 mg and this amount may be given in a single or multiple doses per day or per dose or per cycle of treatment. Dosing regimens may vary significantly and will be determined and altered based on clinical experience with the compound. The full spectrum of dosing regimens may be employed ranging from continuous dosing (with daily doses) to intermittent dosing. A therapeutically effective amount of a pharmaceutically acceptable salt of a compound disclosed herein may be determined as a proportion of the therapeutically effective amount of the compound as the free base. It is envisaged that similar dosages would be appropriate for treatment of the susceptible neoplasms described above.

Compounds disclosed herein may also be used alone or in combination with a B-Raf inhibitor or agonist in the treatment of conditions inhibited or attenuated by inhibition of a Raf family kinase (particularly B-Raf). Further provided are methods for treating a condition attenuated by inhibition of a Raf family kinase (particularly B-Raf) in a mammal in need thereof, comprising administering to the mammal, a therapeutically effective amount of a compound disclosed herein. Also provided is the use of a compound disclosed herein for the preparation of a medicament for the treatment of a condition attenuated by inhibition of a Raf family kinase (particularly B-Raf) in a mammal. Conditions attenuated by inhibition of a Raf family kinase (including B-Raf) include but are not limited to neoplasms.

In the above-described methods of treatment and uses, a compound disclosed herein may be employed alone, in combination with one or more other compounds disclosed herein or in combination with other therapeutic methods or agents. In particular, in methods of treating a condition attenuated by combination with other chemotherapeutic, biologic, hormonal, antibody and supportive care agents is envisaged as well as combination with surgical therapy and radiotherapy. Supportive care agents include analgesics, anti-emetics and agents used to treat heamatologic side effects such as neutropenia. Analgesics are well known in the art. Anti-emetics include but are not limited to 5HT3 antagonists such as ondansetron, granisetron, dolasetron, palonosetron and the like; prochlorperazine; metoclopramide; diphenhydramine; promethazine; dexamethasone; lorazepam; haloperidol; dronabinol; olanzapine; and neurokinin-1 antagonists such as aprepitant, fosaprepitant and casopitant administered alone or in various combinations.

Combination therapies according to the disclosure thus comprise the administration of at least one compound disclosed herein and the use of at least one other treatment method. In one embodiment, combination therapies according to the disclosure comprise the administration of at least one compound disclosed herein and surgical therapy. In one embodiment, combination therapies according to the disclosure comprise the administration of at least one compound disclosed herein and radiotherapy. In one embodiment, combination therapies according to the disclosure comprise the administration of at least one compound disclosed herein and at least one supportive care agent (e.g., at least one anti-emetic agent). In one embodiment, combination therapies according to the present disclosure comprise the administration of at least one compound disclosed herein and at least one other chemotherapeutic agent. In one particular embodiment, the disclosure comprises the administration of at least one compound disclosed herein and at least one anti-neoplastic agent.

As an additional aspect, the present disclosure provides the methods of treatment and uses as described above, which comprise administering a compound disclosed herein together with at least one chemotherapeutic agent. In one particular embodiment, the chemotherapeutic agent is an anti-neoplastic agent. In another embodiment, the disclosure provides a pharmaceutical composition comprising a compound disclosed herein further comprising at least one other chemotherapeutic agent, more particularly, the chemotherapeutic agent is an anti-neoplastic agent. The disclosure also provides methods of treatment and uses as described above, which comprise administering a compound disclosed herein together with at least one supportive care agent (e.g., antiemetic agent).

The compounds disclosed herein and at least one additional anti-neoplastic or supportive care therapy may be employed in combination concomitantly or sequentially in any therapeutically appropriate combination. The administration of a compound disclosed herein with one or more other anti-neoplastic agents may be in combination in accordance with the disclosure by administration concomitantly in one unitary pharmaceutical composition including both or all compounds or two or more separate pharmaceutical compositions each including one or more of the compounds. The components of the combination may be administered separately in a sequential manner wherein one active ingredient is administered first and the other(s) second or vice versa. Such sequential administration may be close in time or remote in time.

When a compound disclosed herein is used in combination with an anti-neoplastic and/or supportive care agent, the dose of each compound may differ from that when the compound is used alone. Appropriate doses will be readily appreciated by those skilled in the art. The appropriate dose of the compound(s) disclosed herein and the other therapeutically active agent(s) and the relative timings of administration will be selected in order to achieve the desired combined therapeutic effect, and are within the expertise and discretion of the attendant clinician.

Typically, any chemotherapeutic agent that has activity against a susceptible neoplasm being treated may be utilized in combination with the compounds disclosed herein, provided that the particular agent is clinically compatible with therapy employing a compound disclosed herein. Typical anti-neoplastic agents useful in the present disclosure include, but are not limited to: alkylating agents, antimetabolites, antitumor antibiotics, antimitotic agents, topoisomerase I and II inhibitors, hormones and hormonal analogues; retinoids, signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Alkylating agents are non-phase specific anti-neoplastic agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Alkylating agents may be employed in combination with the compounds disclosed herein in the compositions and methods described above. Examples of alkylating agents include but are not limited to nitrogen mustards such as cyclophosphamides, temozolomide, melphalan, and chlorambucil; oxazaphosphorines; alkyl sulfonates such as busulfan; nitrosoureas such as carmustine; triazenes such as dacarbazine; and platinum coordination complexes such as cisplatin, oxaliplatin and carboplatin.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. The end result of discontinuing S phase is cell death. Antimetabolite neoplastic agents may be employed in combination with the compounds disclosed herein in the compositions and methods described above. Examples of antimetabolite anti-neoplastic agents include but are not limited to purine and pyrimidine analogues and anti-folate compounds, and more specifically, hydroxyurea, cytosine, arabinoside, ralitrexed, tegafur, fluorouracil (e.g., 5FU), methotrexate, cytarabine, mercaptopurine and thioguanine.

Antitumor antibiotic agents are non-phase specific agents, which bind to or intercalate with DNA. Typically, such action disrupts ordinary function of the nucleic acids, leading to cell death. Antitumor antibiotics may be employed in combination with the compounds disclosed herein in the compositions and methods described above. Examples of antitumor antibiotic agents include, but are not limited to, actinomycins such as dactinomycin; anthracyclines such as daunorubicin, doxorubicin, idarubicin, epirubicin and mitoxantrone; mitomycin C and bleomycins.

Antimicrotubule or antimitotic agents are phase specific agents active against the microtubules of tumor cells during M or the mitosis phase of the cell cycle. Antimitotic agents may be employed in combination with the compounds disclosed herein in the compositions and methods described above. Examples of antimitotic agents include, but are not limited to, diterpenoids, *vinca* alkaloids, polo-like kinase (Plk) inhibitors and CenpE inhibitors. Examples of diterpenoids include, but are not limited to, paclitaxel and its analog docetaxel. Examples of *vinca* alkaloids include, but are not limited to, vinblastine, vincristine, vindesine and vinorelbine. Plk inhibitors are discussed further below.

Topoisomerase inhibitors include inhibitors of Topoisomerase II and inhibitors of Topoisomerase I. Topoisomerase II inhibitors, such as epipodophyllotoxins, are anti-neoplastic agents derived from the mandrake plant, that typically affect cells in the S and G2 phases of the cell cycle by forming a ternary complex with topoisomerase II and DNA, causing DNA strand breaks. The strand breaks accumulate and cell death follows. Examples of epipodophyllotoxins include, but are not limited to, etoposide and teniposide. Camptothecins, including camptothecin and camptothecin derivatives, are available or under development as Topoisomerase I inhibitors. Examples of camptothecins include, but are not limited to amsacrine, irinotecan, topotecan, and the various optical forms of 7-(4-methylpiperazino-methylene)-10,11-ethylenedioxy-20-camptothecin. Topoisomerase inhibitors may be employed in combination with the compounds disclosed herein in the compositions and methods described above.

Hormones and hormonal analogues are useful compounds for treating cancers in which there is a relationship between the hormone(s) and growth and/or lack of growth of the cancer. Antitumor hormones and hormonal analogues may be employed in combination with the compounds disclosed herein in the compositions and methods described above. Examples of hormones and hormonal analogues believed to be useful in the treatment of neoplasms include, but are not limited to antiestrogens, such as tamoxifen, toremifene, raloxifene, fulvestrant, idoxifene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrozole, vorozole, and exemestane; progestrins such as megestrol acetate; 5-alpha-reductase inhibitors such as finasteride and dutasteride; and gonadotropin-releasing hormones (GnRH) and analogues thereof, such as Luteinizing Hormone-releasing Hormone (LHRH) agonists and antagonists such as goserelin, leuprolide, leuprorelin and buserelin.

Examples of specific retinoids that may be used in combination with the compounds disclosed herein include: retinoic acid; all-trans-retinoic acid ("ATRA" also known as "tretinoin"); tamibarotene ("Am80"); 9-cis-retinoic acid ((2E,4E,6Z,8E)-3,7-Dimethyl-9-(2,6,6-trimethylcyclohex-1-enyl)nona-2,4,6,-8-tetraenoic Acid) (also known as "9-cis-Tretinoin") (available from Sigma); Isotretinoin ((2Z,4E,6E,8E)-3,7-dimethyl-9-(2,6,6-trimethyl-1-cyclohexenyl)nona-2,4,6,-8-tetraenoic acid) (also known as "13-cis-retinoic acid") (ACCUTANE™); Am580 (4-(5,6,7,8-tetrahydro-5,5,8,8-tetramethyl-2-naphtamido) benzoic acid), See, M. Gianni, Blood 1996 87(4):1520-1531; TTNPB (4-[E-2-(5,6,7,8-Tetrahydro-5,5,8,8-tetramethyl-2-naphthalenyl)-1-propeny-1]benzoic acid) (also known as "Ro 13-7410") See, M. F. Boehm et al. J. Med. Chem. 1994 37:2930 and R. P. Bissonnette et al., Mol. Cell. Biol. 1995 15:5576; and BMS753 (4-[[(2,3-dihydro-1,1,3,3-tetramethyl-2-oxo-1H-inden-5-yl)carbonyl]amino]-benzoic acid) See, U.S. Pat. No. 6,184,256.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds disclosed herein in any of the compositions and methods/uses described herein. Trastuzumab is an example of an anti-erbB2 antibody inhibitor of growth factor function. One example of an anti-erbB1 antibody inhibitor of growth factor function is cetuximab. Bevacizumab is an example of a monoclonal antibody directed against VEGFR. Examples of small molecule inhibitors of epidermal growth factor receptors include but are not limited to lapatinib and erlotinib. Imatinib is one example of a PDGFR inhibitor. Examples of VEGFR inhibitors include pazopanib, ZD6474, AZD2171, PTK787, sunitinib and sorafenib.

In certain embodiments, compounds disclosed herein can be used and formulated in combination with the anti-cancer agents that are PD-1 antibodies such as nivolumab, pembrolizumab, pidilizumab, atezolizumab or CTLA-4 antibodies such as ipilimumab and tremelimumab.

Pharmaceutical Compositions

While it is possible that, for use in therapy, a therapeutically effective amount of a compound disclosed herein may be administered as the raw chemical, it is typically presented as the active ingredient of a pharmaceutical composition or formulation. Accordingly, the disclosure further provides a pharmaceutical composition comprising a compound disclosed herein. The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound disclosed herein with one or more pharmaceutically acceptable carriers, diluents and/or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound disclosed herein (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

Pharmaceutical formulations adapted for oral administration may be presented as discrete units such as liquid-filled or solid capsules; immediate, delayed or controlled release tablets; powders or granules; solutions or suspensions in aqueous or non-aqueous liquids; edible foams or whips; oil-in-water liquid emulsions, water-in-oil liquid emulsions or oral strips, such as impregnated gel strips.

For instance, for oral administration in the form of a tablet or capsule, the active drug component can be combined with an oral pharmaceutically acceptable carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Solid capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds disclosed herein can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Solutions and syrups can be prepared by dissolving the compound in a suitably flavored aqueous solution, while elixirs are prepared through the use of a pharmaceutically acceptable alcoholic vehicle. Suspensions can be formulated by dispersing the compound in a pharmaceutically acceptable vehicle. Solubilizers and emulsifiers such as ethoxylated isostearyl alcohols and polyoxyethylene sorbitol ethers, preservatives, flavor additive such as peppermint oil or natural sweeteners or saccharin or other artificial sweeteners, and the like can also be added.

Where appropriate, unit dosage formulations for oral administration can be microencapsulated. The formulation can also be prepared to prolong or sustain the release as for example by coating or embedding particulate material in polymers, wax or the like.

The compounds of the disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the disclosure may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polycentric acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research (1986) 3(6):318.

Pharmaceutical formulations adapted for topical administration may be formulated as ointments, creams, suspensions, lotions, powders, solutions, pastes, gels, sprays, aerosols or oils. For treatments of external tissues, such as skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, metered dose inhalers, dry powder inhalers, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation of pharmaceutically acceptable tonicity with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavoring agents.

Examples

High Dietary Fat Elevates Serum Acetoacetate to Promote BRAF V600E Tumor Growth

Figure 1C:
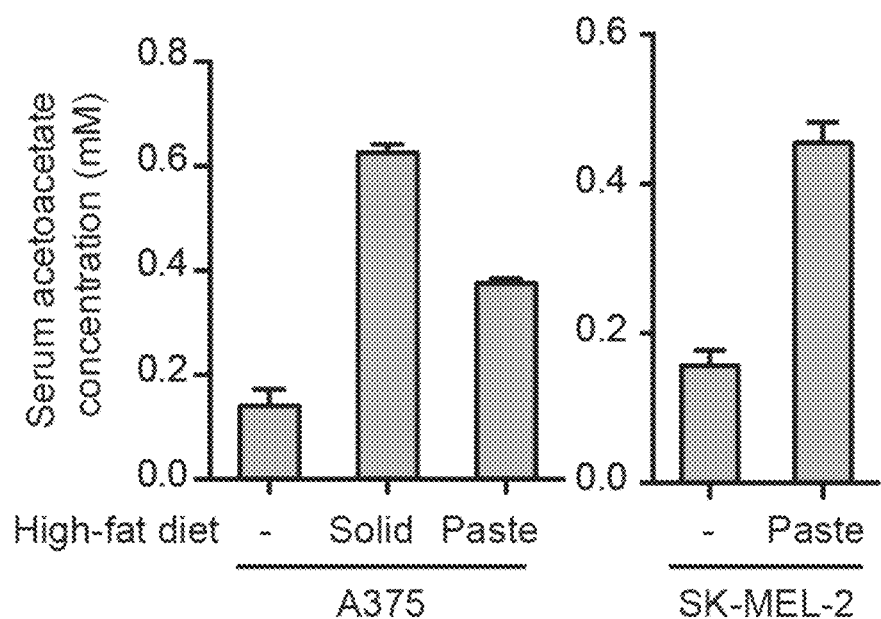
FIG. 1C shows data on acetoacetate (AA), levels in serum harvested from A375 and SK-MEL-2 xenograft mice fed with normal or different high-fat diets.
Figure 1D:
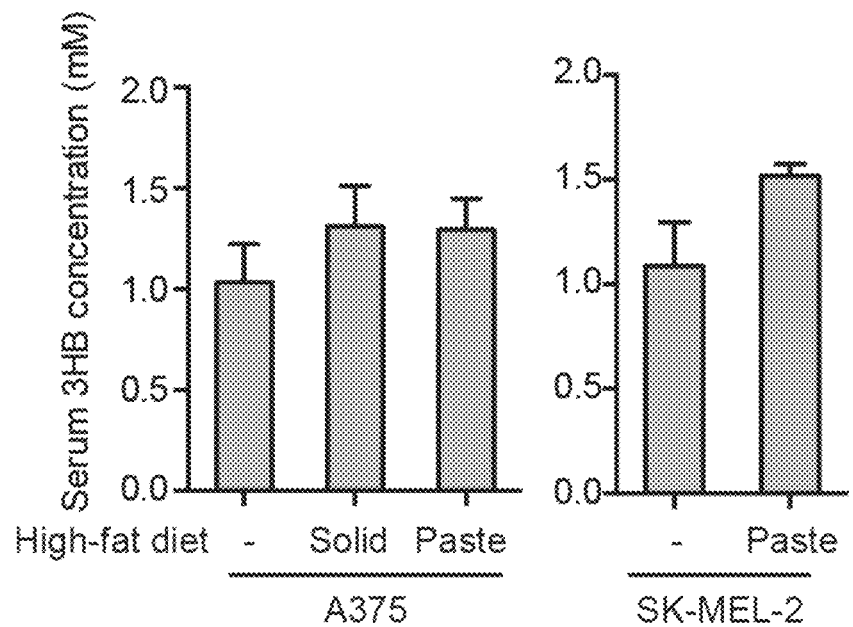
FIG. 1D shows data for β-hydroxybutyrate (3HB).
Figure 1E:
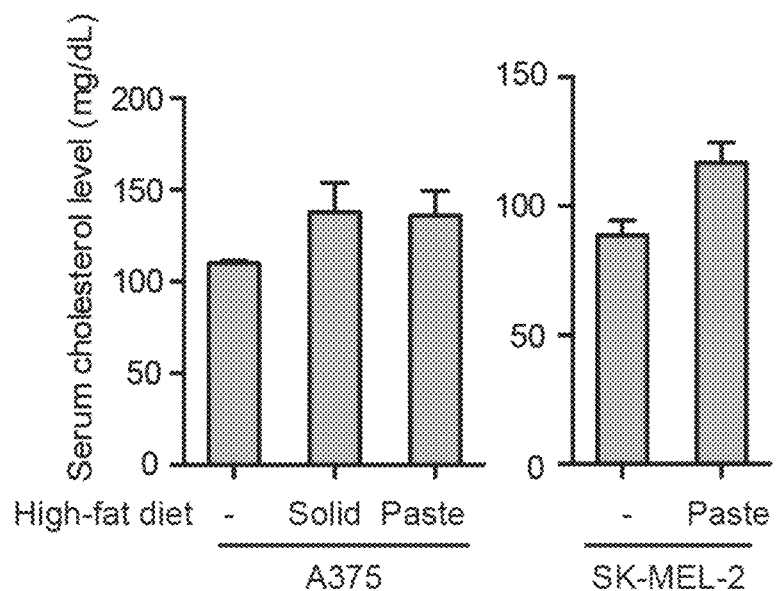
FIG. 1E shows data for cholesterol.
Figure 1F:
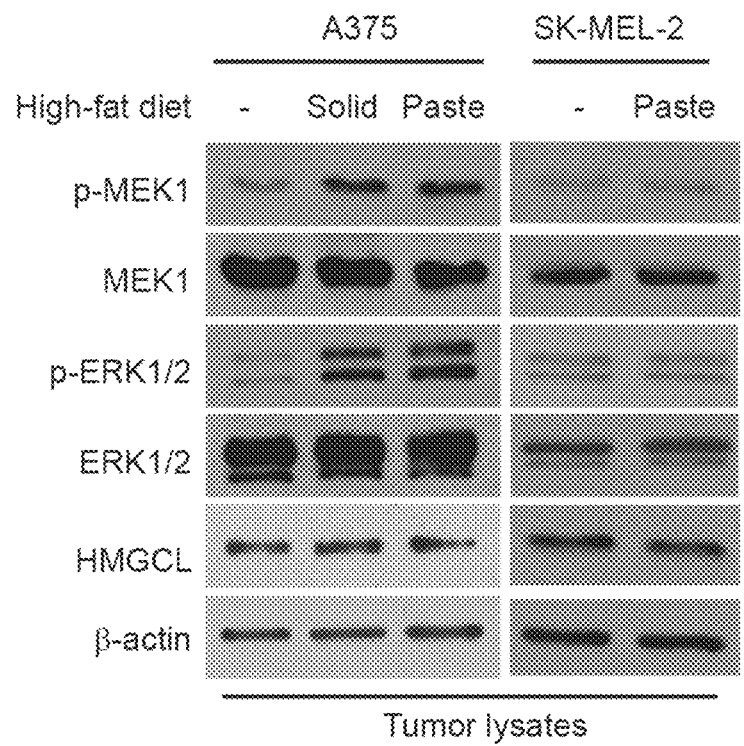
FIG. 1F shows western blot results show MEK1 and ERK1/2 phosphorylation in tumor tissue samples obtained from xenograft mice.
Figure 1G:
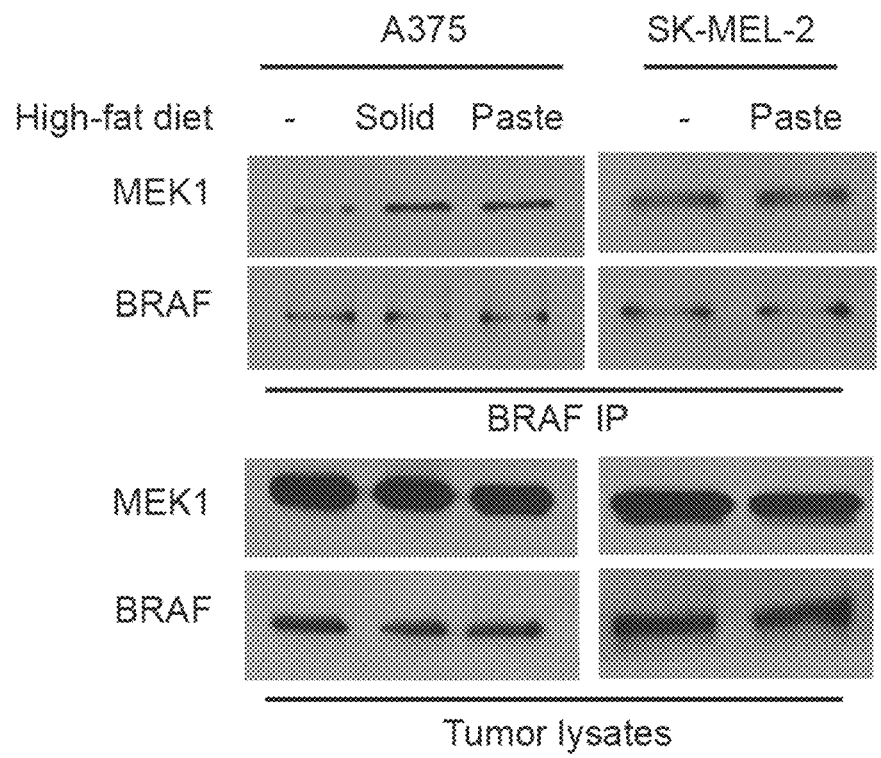
FIG. 1G shows data for BRAF-MEK1 binding (F).
Figure 1H:
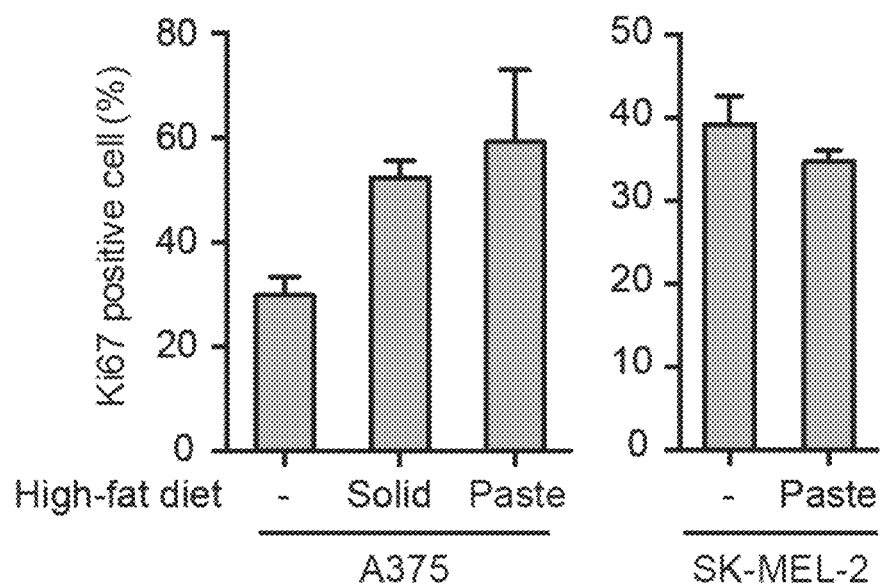
FIG. 1H shows results of immunohistochemical (IHC) staining assay detecting Ki67-positive cells in tumor tissue samples from A375 and SK-MEL-2 xenograft mice.

High-fat diets in either solid or paste forms resulted in increased growth rates, masses and sizes of tumor xenografts without affecting body weight in nude mice inoculated with BRAF V600E-expressing human melanoma A375 cells (FIGS. 1A and B). In contrast, a high-fat diet did not affect tumor growth rates, masses or sizes or body weight in mice inoculated with control SK-MEL-2 cells expressing an active NRAS Q61R mutant. This was not due to differences in food intake amounts, but likely due to increased serum levels of acetoacetate in both groups of mice fed with high-fat diets (FIG. 1C). Consumption of a high-fat diet did not significantly affect serum levels of D-β-hydroxybutyrate (3HB) (Figure D, but significantly increased serum cholesterol levels (FIG. 1E) and reduced serum glucose levels, compared to control mice fed with normal food. The increased serum levels of acetoacetate led to enhanced phosphorylation of MEK1 and ERK1/2 without affecting HMGCL expression (FIG. 1F), as well as increased binding between BRAF V600E-MEK1 (FIG. 1G) in tumors derived from A375 cells but not control SK-MEL-2 cells, compared to corresponding control xenograft mice fed with normal food. Consistent with these findings, consumption of a high-fat diet resulted in increased cell proliferation rates in tumors derived from A375 cells but not control SK-MEL-2 cells, assessed by increased immunohistochemistry (IHC) staining of Ki67, compared to corresponding control xenograft mice fed with normal food (FIG. 1H). Similar results were obtained in nude mice inoculated with BRAF V600E-expressing human melanoma A2058 cells compared to mice inoculated with control PMWK cells expressing BRAF wild-type (WT) or HMCB cells expressing an active NRAS Q61K mutant.

Figure 2A:
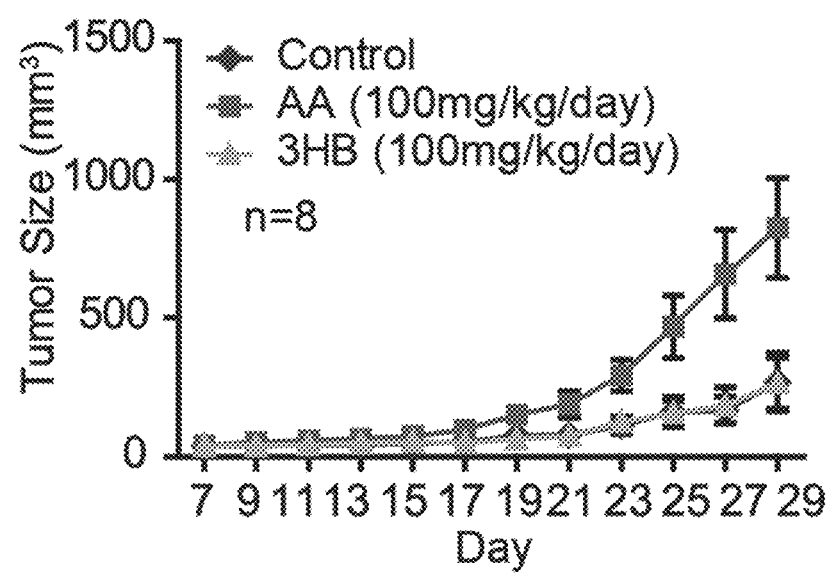
FIG. 2A shows data indicating intraperitoneally injected acetoacetate selectively promotes BRAF V600E positive melanoma tumor growth in nude mice inoculated with human melanoma BRAF V600E-positive A375 cells and intraperitoneally injected with AA or 3HB.
Figure 2B:
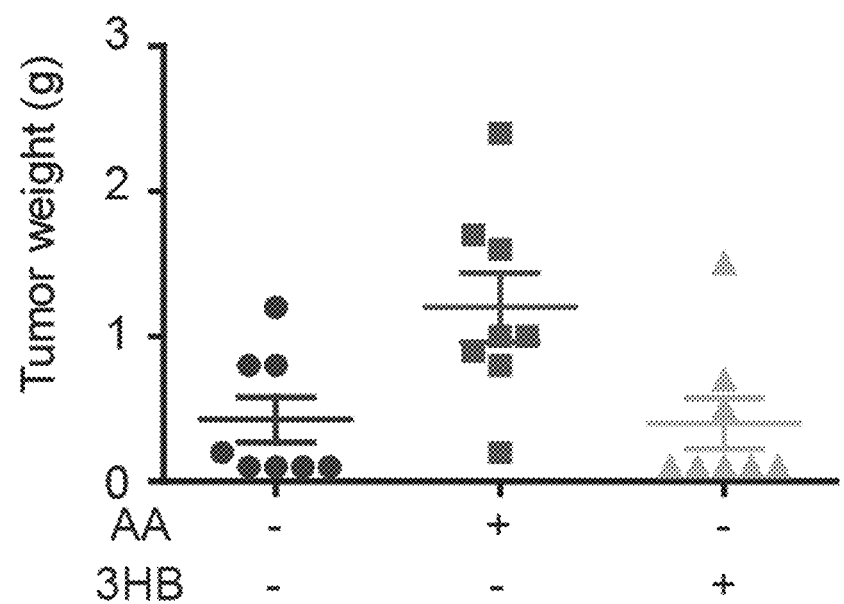
FIG. 2B shows data on tumor weight.

Intraperitoneal Injection with Acetoacetate but not 3HB Promotes BRAF V600E Tumor Growth Intraperitoneal injection with acetoacetate but not 3HB resulted in increased growth rates and masses of xenograft tumors in nude mice inoculated with BRAF V600E expressing A375 melanoma cells (FIG. 2A). In contrast, injection with either acetoacetate or 3HB had no effect on growth rates or masses of tumor xenografts in mice inoculated with control NRAS Q61K-expressing HMCB cells.

The lithium salt form of acetoacetate was used, which provides the anion form of acetoacetate that is approximately 55 times more stable with a half-life of 130 hours than the acid form (acetoacetic acid) with a half-life of 140 minutes at 37° C. in water. To exclude potential effects of the lithium ion, a series of experiments were performed using a control salt lithium chloride. Lithium chloride did not bind to purified BRAF V600E in a thermal shift assay or promote the association between purified BRAF V600E and MEK1 as acetoacetate does. Consistently, treatment with lithium chloride did not affect phosphorylation levels of MEK1 or ERK1/2, BRAF V600E-MEK1 binding, or cell proliferation rates in diverse BRAF V600E positive or negative human melanoma cells. Moreover, lithium chloride treatment did not affect tumor growth potential of BRAF V600E-expressing A375 cells in xenograft mice in vivo, nor did it affect serum levels of acetoacetate, 3HB, cholesterol or glucose, phosphorylation levels of MEK1 or ERK1/2, BRAF V600E-MEK1 binding, or cell proliferation potential in tumors derived from A375 cells in xenograft mice.

In addition, similar studies were performed to exclude possible effects from the potential degradation product of acetoacetate, acetone. Acetone did not bind to purified BRAF V600E or affect the association between purified BRAF V600E and MEK1. Acetone also did not affect phosphorylation levels of MEK1 or ERK1/2, BRAF V600E-MEK1 binding, or cell proliferation rates in diverse BRAF V600E positive or negative human melanoma cells. These results, together with finding that $^{14}C$ labeled acetoacetate (lithium salt form) binds to purified BRAF V600E, suggest that the anion form of acetoacetate is the functional compound that binds to and regulates BRAF V600E.

Figure 2C:
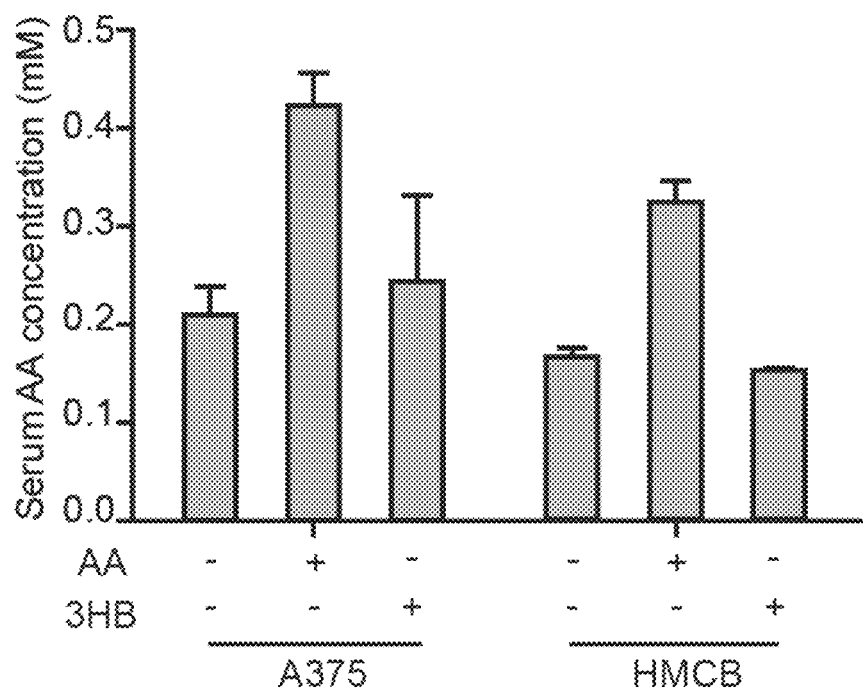
FIG. 2C shows data on AA levels in serum harvested from A375 and HMCB xenograft mice treated with AA.
Figure 2D:
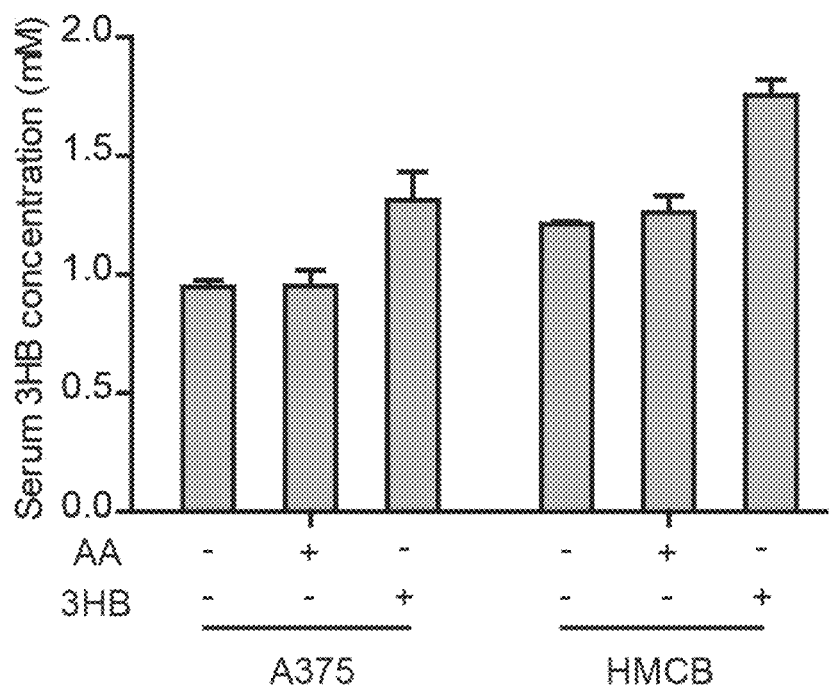
FIG. 2D shows data on 3HB.
Figure 2E:
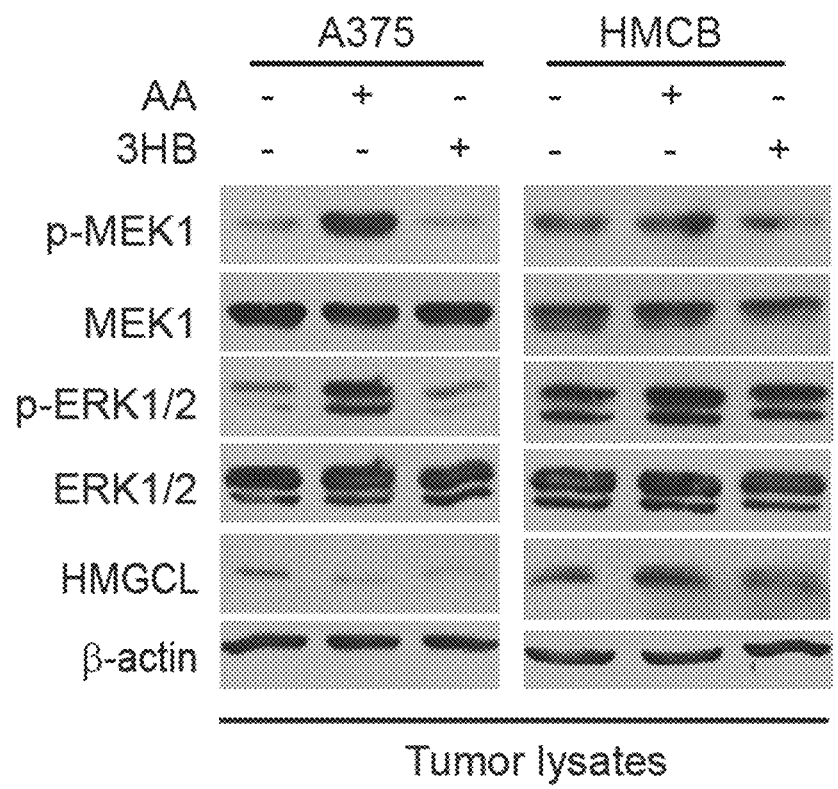
FIG. 2E shows western blot results show MEK1 and ERK1/2 phosphorylation in tumor tissue samples obtained from xenograft mice.
Figure 2F:
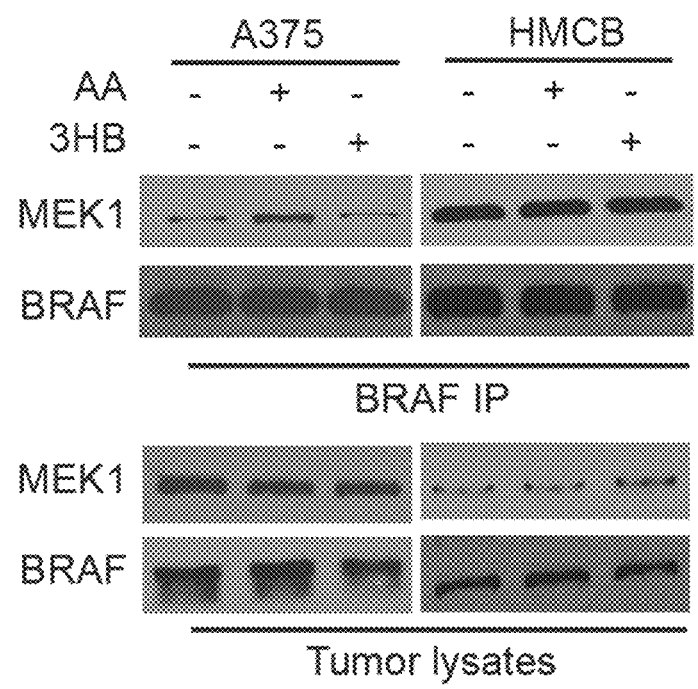
FIG. 2F shows data on BRAF-MEK1 binding.
Figure 2G:
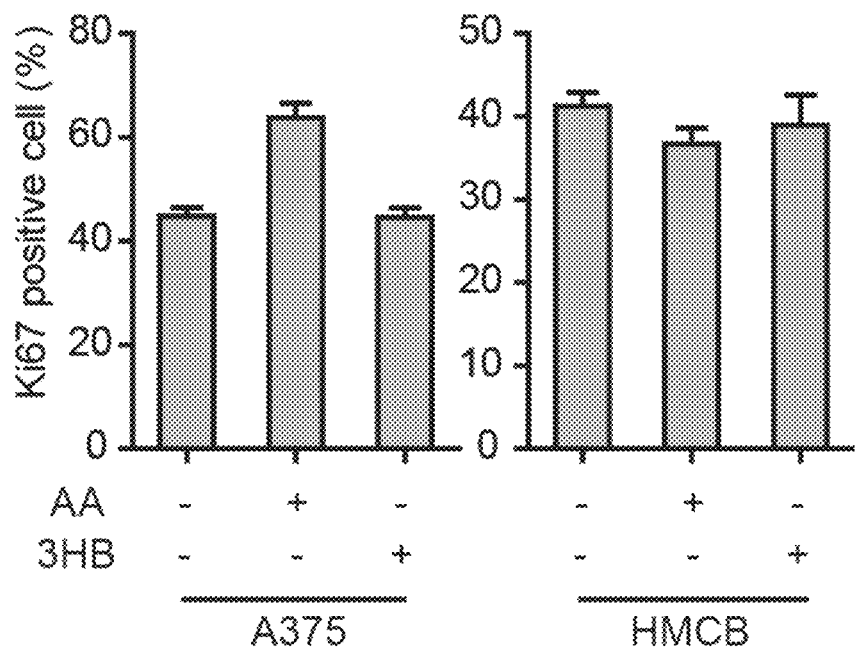
FIG. 2G shows results of IHC staining assay detecting Ki67-positive cells in tumor tissue samples from xenograft mice.

Intraperitoneal injection with acetoacetate led to increased serum levels of acetoacetate (FIG. 2C) but did not affect serum levels of 3HB (FIG. 2D), whereas 3HB injection increased serum levels of β-hydroxybutyrate (FIG. 2D) but not acetoacetate (FIG. 2C). Similarly, chronic injection of acetoacetate or 3HB to nude mice for 4 weeks resulted in increased serum acetoacetate but not 3HB levels or increased 3HB but not acetoacetate levels, respectively. Such chronic treatments to mice did not alter the acetoacetate or 3HB levels in urine, suggesting the dosages of acetoacetate and 3HB were insufficient to induce acidosis in mice. Moreover, in mice inoculated with A375 cells, injection with acetoacetate but not 3HB resulted in enhanced phosphorylation of MEK1 and ERK1/2 (FIG. 2E), enhanced BRAF V600E-MEK1 association (FIG. 2F), increased tumor sizes, and enhanced cell proliferation rates assessed by increased Ki67 IHC staining (FIG. 2G). In contrast, in mice inoculated with HMCB cells, injection of either acetoacetate or β-hydroxybutyrate did not affect MEK-ERK activation (FIG. 2D), BRAF-MEK1 binding (FIG. 2F) or cell proliferation rates (FIG. 2G) in harvested tumors. Together, these data suggest that dietary fat likely promotes tumor growth potential of BRAF V600E-expressing melanoma cells in vivo through elevation of serum levels of acetoacetate.

Hypolipidemic Agents Attenuate BRAF V600E Tumor Growth by Reducing Serum Levels of Acetoacetate Whether treatment with hypolipidemic agents may attenuate circulating acetoacetate levels and consequently BRAF V600E tumor growth potential in mice was examined. Three drugs were chosen that are clinically used to treat hypercholesterolemia, including fluvastatin that belongs to a class of cholesterol-lowering statins as HMG-CoA reductase inhibitors; niacin (vitamin B3) that lowers triglycerides and is also clinically used to treat cardiovascular patients not taking a statin and fenofibrate, a fibric acid derivative that also lowers triglycerides.

Figure 3A:
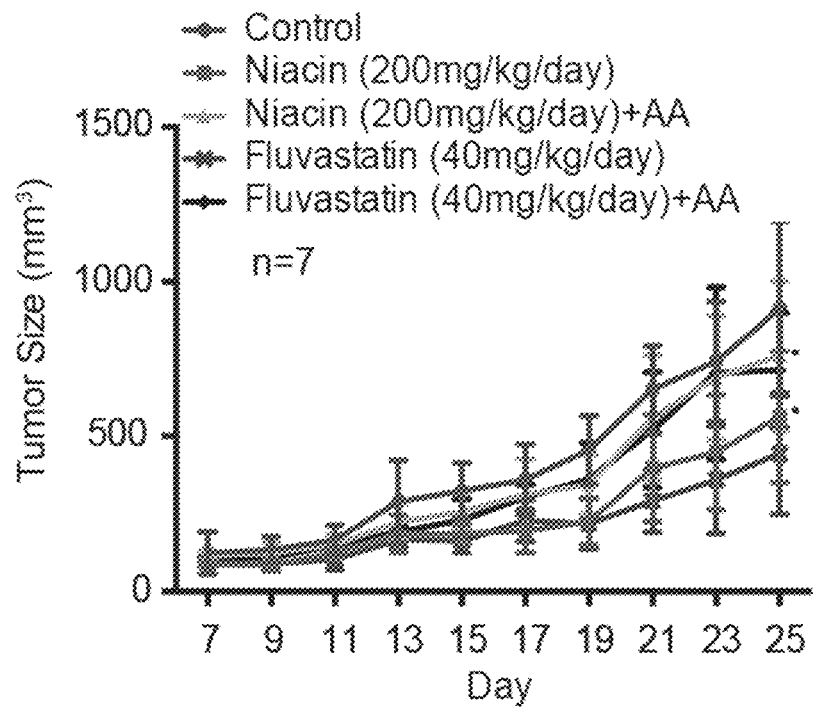
FIG. 3A shows data indicating lipid lowering agents decrease serum acetoacetate levels in xenograft mice and reduce BRAF V600E tumor growth xenograft tumor growth (left) in nude mice inoculated with human melanoma BRAF V600E-positive A375 cells and orally treated with two different lipid lowering agents, niacin or fluvastatin, alone or in combination with intraperitoneal injection with acetoacetate (AA).
Figure 3B:
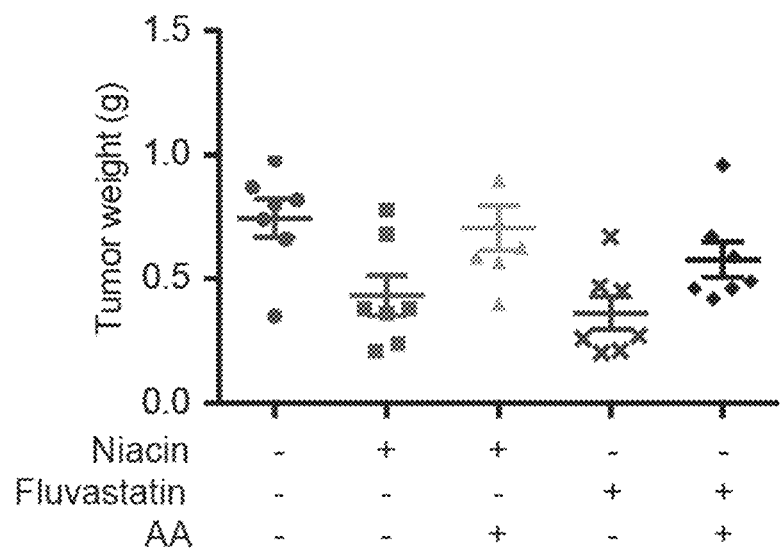
FIG. 3B shows data on weight.
Figure 3C:
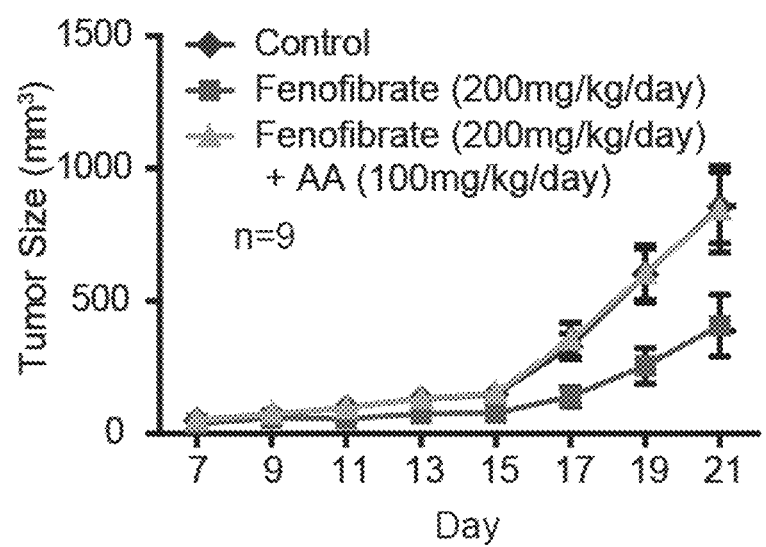
FIG. 3C shows tumor growth in nude mice inoculated with human melanoma BRAF V600E-positive A2058 and orally treated with lipid lowering agent fenofibrate alone or in combination with intraperitoneal injection with AA.
Figure 3D:
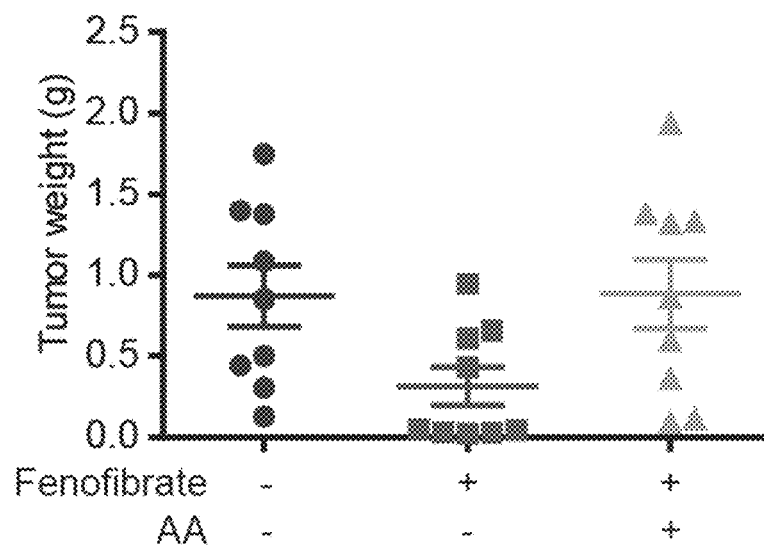
FIG. 3D shows data on weight.
Figure 3E:
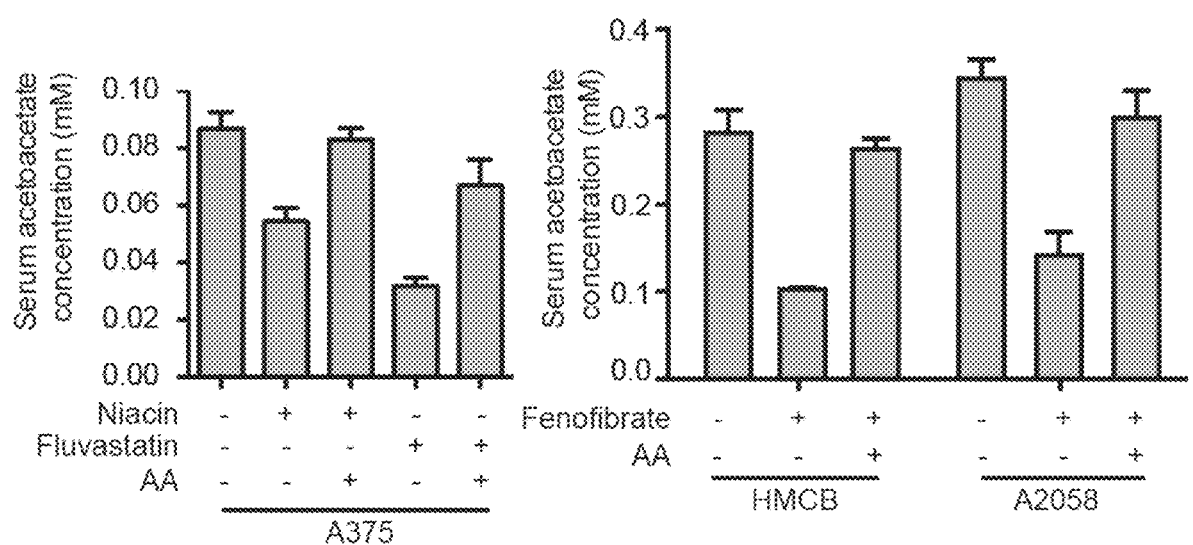
FIG. 3E shows AA levels in serum harvested from A375, A2058 and HMCB xenograft mice tissue.
Figure 3F:
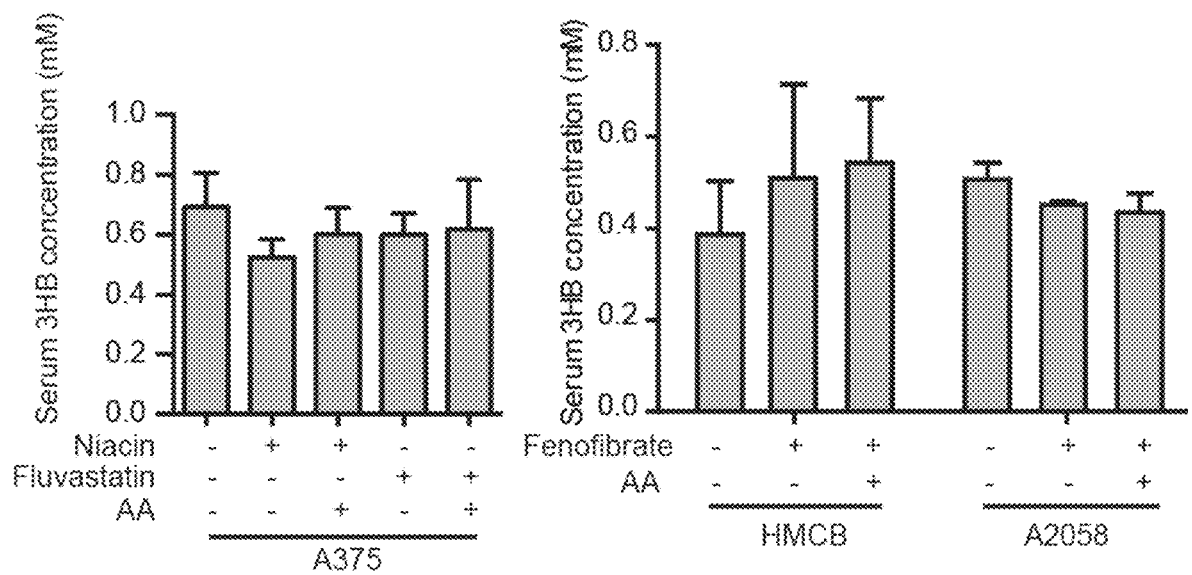
FIG. 3F shows data on 3HB.

Fluvastatin and niacin treatment effectively attenuated tumor growth potential of BRAF V600E-expressing A375 cells in xenograft mice, which could be reversed by intraperitoneal injection with acetoacetate (FIG. 3A). Similarly, treatment with fenofibrate attenuated tumor growth potential of BRAF V600E-expressing A2058 melanoma cells in xenograft nude mice (FIG. 3A), but not control mice inoculated with NRAS Q61K-expressing HMCB cells. Intraperitoneal acetoacetate injection effectively rescued the decreased tumor growth of A2058 cells in mice treated with fenofibrate but had no effect on tumor growth potential of HMCB cells in xenograft mice. Consistent with these findings, treatment with fluvastatin, niacin or fenofibrate resulted in reduced serum levels of acetoacetate but not O-hydroxybutyrate in mice (FIGS. 3E and 3F, respectively), while acetoacetate injection rescued the decreased serum acetoacetate levels but did not affect 3HB levels.

Figure 3G:
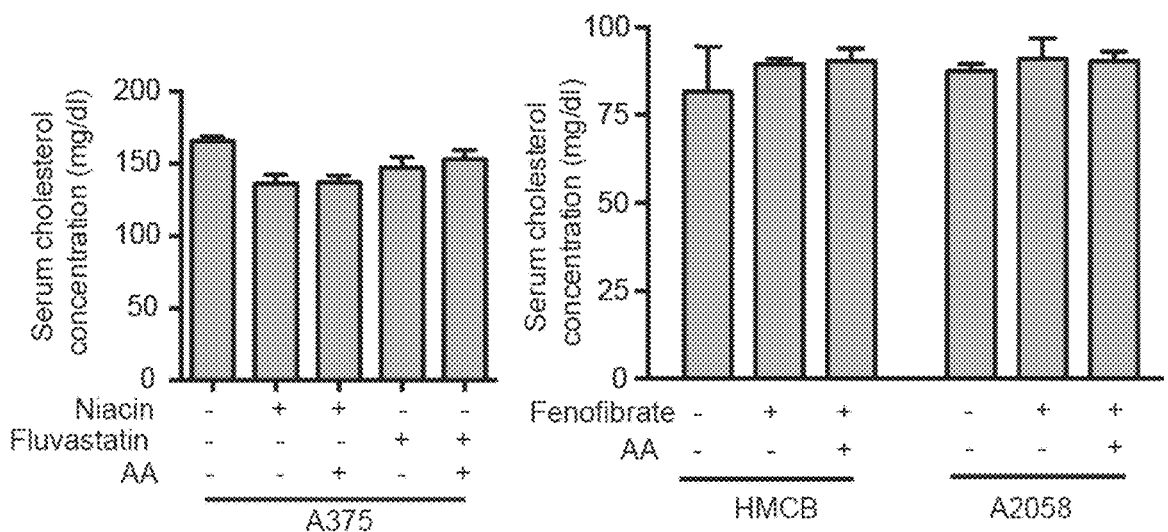
FIG. 3G shows data on cholesterol.
Figure 3H:
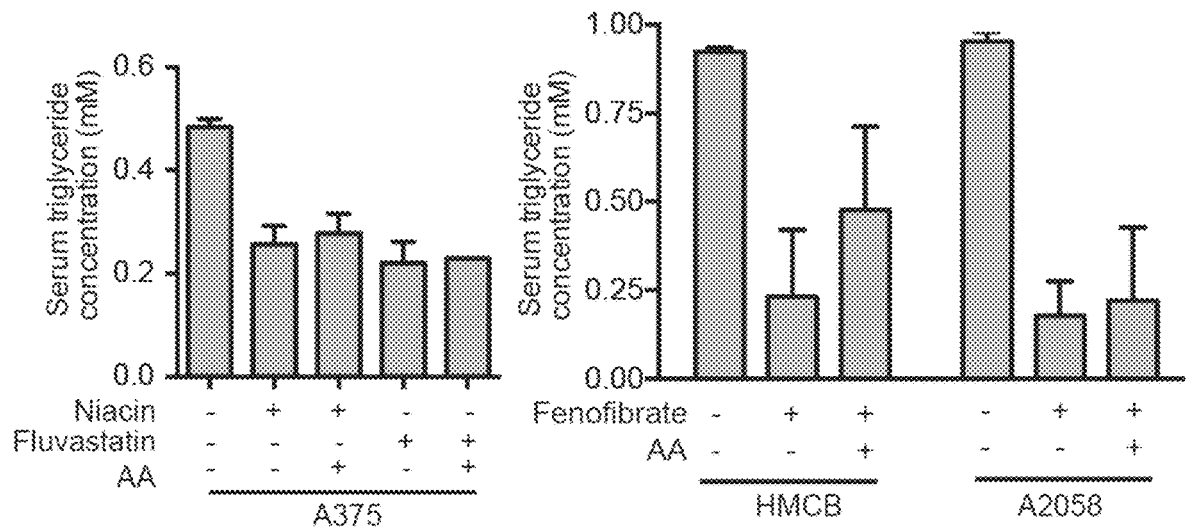
FIG. 3H shows data on triglyceride.
Figure 3I:
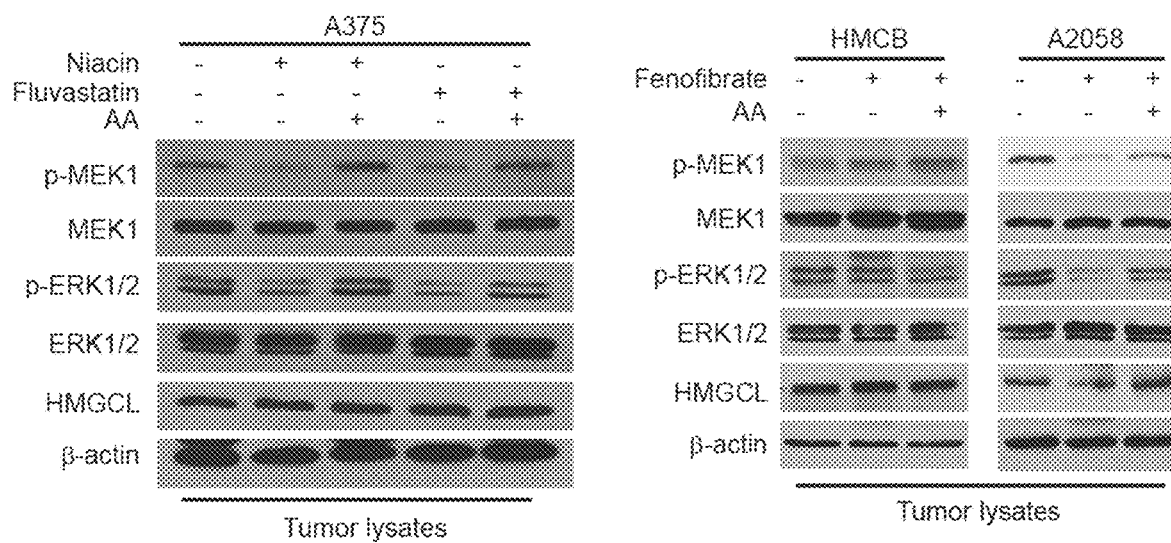
FIG. 3I shows western blot results show MEK1 and ERK1/2 phosphorylation in tumor tissue samples obtained from xenograft mice tissue.
Figure 3J:
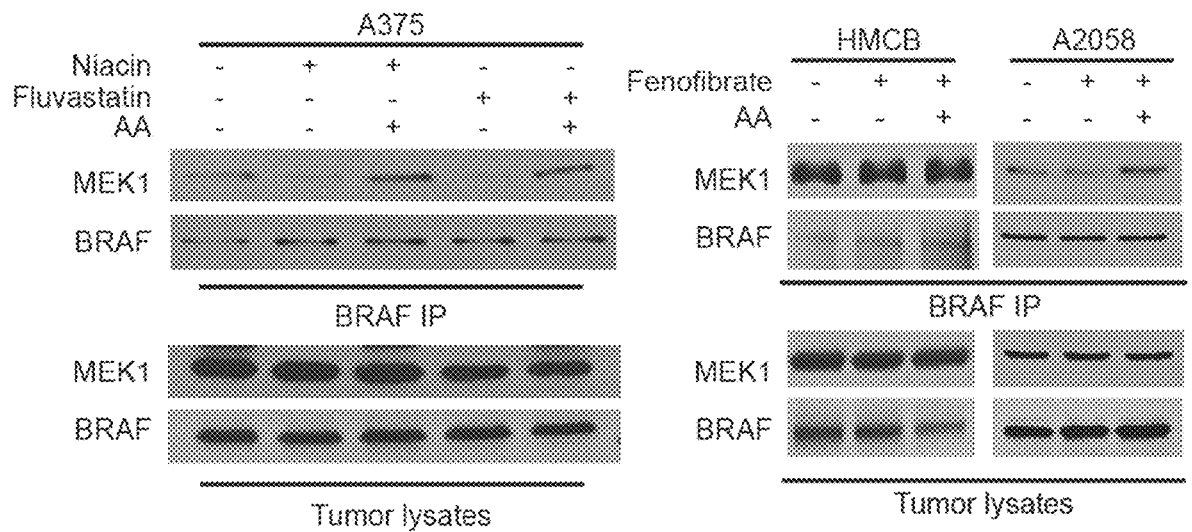
FIG. 3J shows BRAF-MEK1 binding.
Figure 3K:
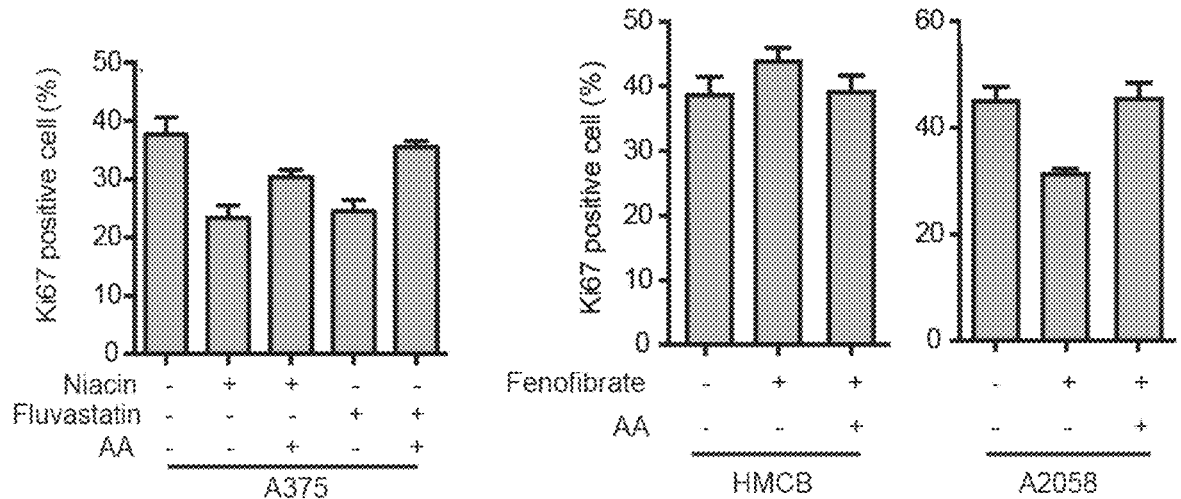
FIG. 3K shows results of IHC staining assay detecting Ki67-positive cells in tumor tissue samples from xenograft mice.

Although these three drugs did not affect serum glucose levels or body weight of mice and only niacin treatment resulted in marginally decreased serum cholesterol levels that were not affected by acetoacetate injection (FIG. 3G), all three hypolipidemic agents effectively reduced serum levels of triglyceride in mice despite acetoacetate injection (FIG. 3H). Consistently, fluvastatin, niacin, or fenofibrate treatment resulted in decreased phosphorylation of MEK1 and ERK1/2 (FIG. 3I), decreased BRAF V600E-MEK1 association (FIG. 3J), and reduced cell proliferation rates as evidenced by decreased Ki67 IHC staining (FIG. 3K) only in tumors derived from BRAF V600E-expressing A375 and A2058 cells but not control HMCB cells, whereas these inhibitory effects were effectively reversed by injection with acetoacetate. Similar results were obtained in fluvastatin or niacin-treated nude mice inoculated with A2058 cells.

Dehydroacetic Acid (DHAA) is an Inhibitory Homologue of Acetoacetate

Figure 4B:
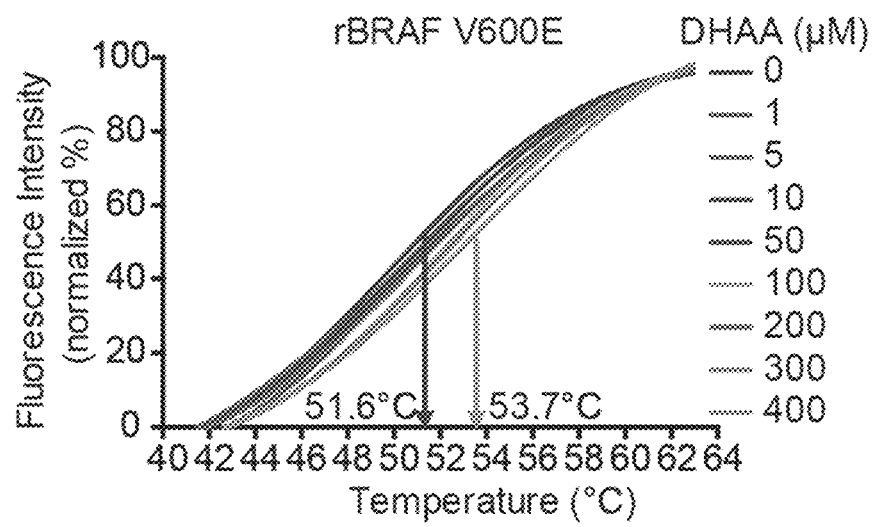
FIG. 4B shows data from a thermal melt shift assay performed to examine the protein (BRAF V600E) and ligand (DHAA) interaction. Arrows in the panel indicate melting temperatures at 0 μM (left) and 400 μM (right).
Figure 4C:
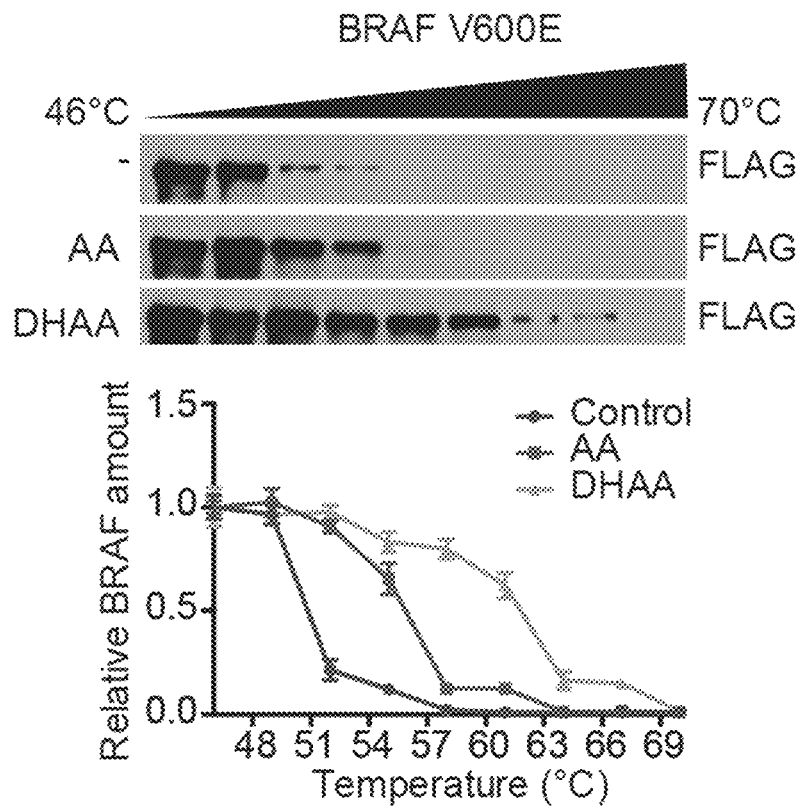
FIG. 4C shows data from an intracellular thermal melt shift assay performed to examine the protein BRAF V600E and ligand (AA or DHAA) interaction.

Whether functional inhibition of acetoacetate would attenuate BRAF V600E tumor growth was examined. Dehydroacetic acid (DHAA) (FIG. 4A) is an inhibitory homologue of acetoacetate. Similar to acetoacetate, DHAA also directly binds to BRAF V600E but not BRAF WT in a thermal melt shift assay using purified recombinant BRAF WT or V600E incubated with increasing concentrations of DHAA (FIG. 4B). Moreover, in a cellular thermal shift assay using cell lysates from 293T cells transfected with FLAG-tagged BRAF WT or V600E, both acetoacetate (400 µM) and DHAA (400 µM) bound only to BRAF V600E but not WT, and DHAA bound to BRAF V600E with higher affinity than acetoacetate (FIG. 4C).

Figure 4D:
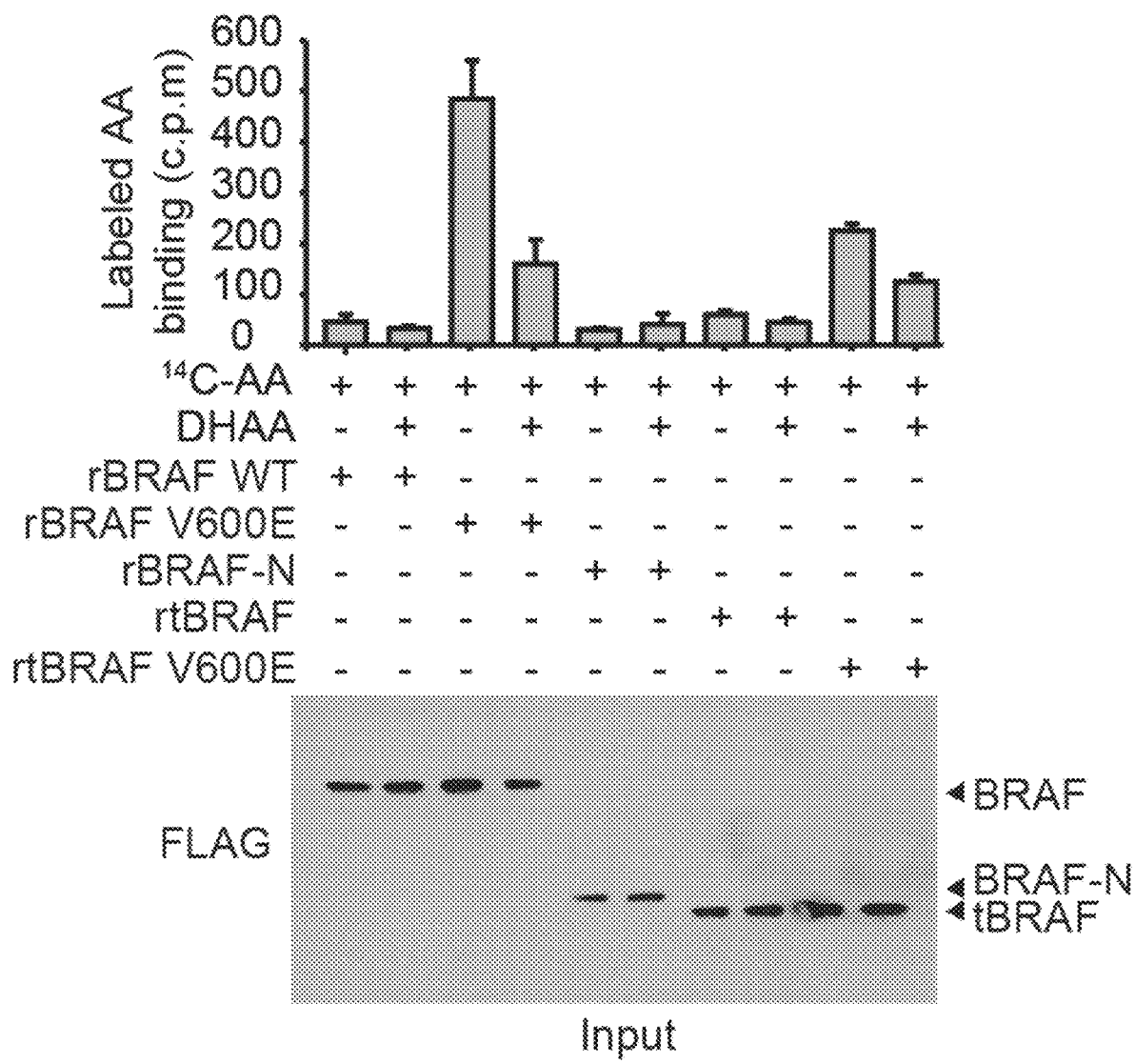
FIG. 4D shows data from a radiometric metabolite-protein interaction analysis using $^{14}$C-labeled acetoacetate incubated with purified BRAF variants, followed by treatment with DHAA.
Figure 4E:
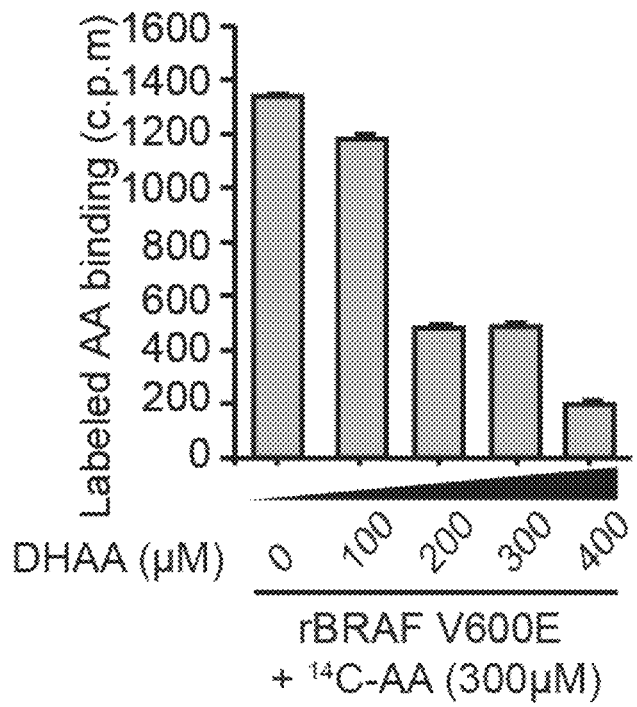
FIG. 4E shows data from a radiometric metabolite-protein interaction analysis using purified recombinant BRAF V600E (rBRAF V600E) pre-treated with $^{14}$C-labeled acetoacetate incubated with increasing of DHAA.
Figure 4F:
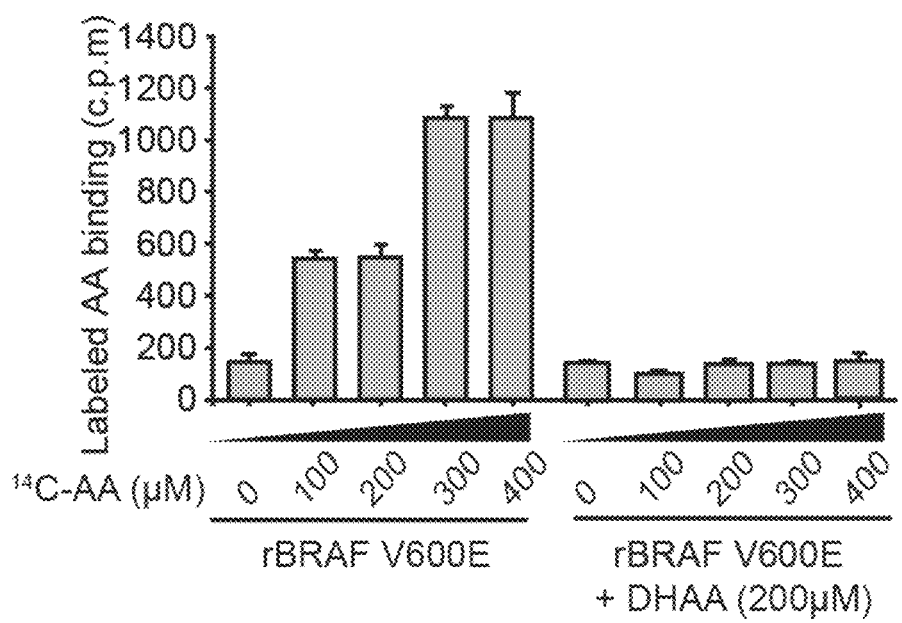
FIG. 4F shows data with rBRAF V600E pre-treated with DHAA incubated with increasing concentrations of $^{14}$C-labeled acetoacetate.
Figure 4G:
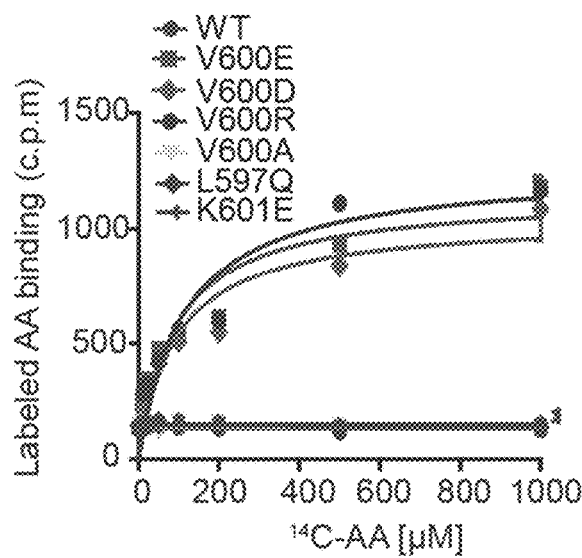
FIG. 4G shows Kd values (left) determined by a $^{14}$C-labeled acetoacetate binding assay. BRAF wild type and mutant proteins were incubated with increasing concentrations of $^{14}$C-labeled acetoacetate. Effect of increasing concentrations of DHAA on $^{14}$C-labeled acetoacetate binding to BRAF mutant proteins (right).
Figure 4G:
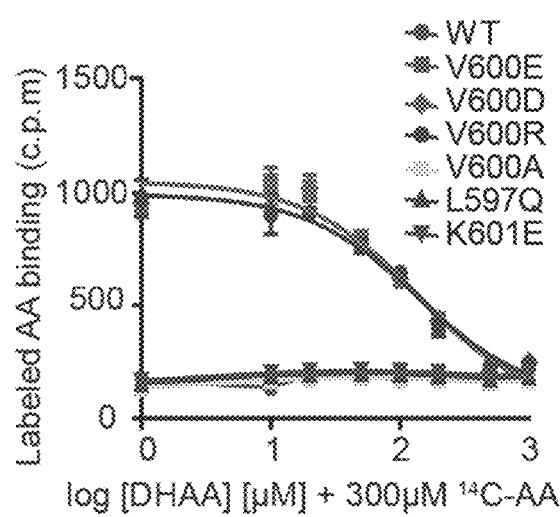

A series of radiometric metabolite-protein interaction analyses were performed using $^{14}C$ labeled acetoacetate incubated with purified BRAF variants in the presence and absence of DHAA. As shown in FIG. 4D, $^{14}C$-labeled acetoacetate specifically bound to BRAF V600E and a V600E mutant of an active, truncated C-terminal domain of BRAF (tBRAF, 416-766 aa), but not to control proteins including BRAF WT, tBRAF WT or a truncated N-terminal domain of BRAF (BRAF-N, 1-415 aa), whereas treatment with DHAA resulted in a significant decrease in binding ability of BRAF V600E mutant forms to acetoacetate (FIG. 4D). Additionally, DHAA competed with acetoacetate for BRAF V600E binding in a dose-dependent manner in a binding assay where purified BRAF V600E mutant pre-treated with $^{14}C$-labeled acetoacetate was incubated with increasing concentrations of DHAA (FIG. 4E). Furthermore, pre-treatment of purified BRAF V600E mutant with DHAA (200 µM) was sufficient to block acetoacetate binding to recombinant BRAF V600E incubated with increasing concentrations of $^{14}C$-labeled acetoacetate up to 400 µM (FIG. 4F). These data together suggest that DHAA binds to BRAF V600E with a higher affinity that enables DHAA to compete with acetoacetate for V600E binding. $^{14}C$-Labeled acetoacetate bound only to BRAF proteins harboring different substitutions of V600 including clinically reported V600E, V600D and V600R with Kd values determined as approximately 92 µM, 93 µM and 113 µM, respectively, but not to a negative control mutant V600A or to other clinically reported BRAF mutants including L597Q and K601E (FIG. 4G, left). Moreover, DHAA effectively competed for binding with BRAF V600E, V600D and V600R in the presence of 300 µM 14C-labeled acetoacetate with Ki values determined as approximately 88 µM, 88 µM and 91 µM, respectively (FIG. 4G, right).

These findings are also consistent with results from a binding assay using $^{14}C$-labeled acetoacetate incubated with diverse BRAF mutants, where acetoacetate bound to V600E, V600D and V600R but not to control V600A mutant or other clinically reported BRAF mutants including K507E, N581S, D594N, L597Q, K601E, and S616F, and acetoacetate promoted MEK1 binding to BRAF V600E, V600D and V600R with increased MEK1 phosphorylation, but not to other BRAF mutants.

Figure 4H:
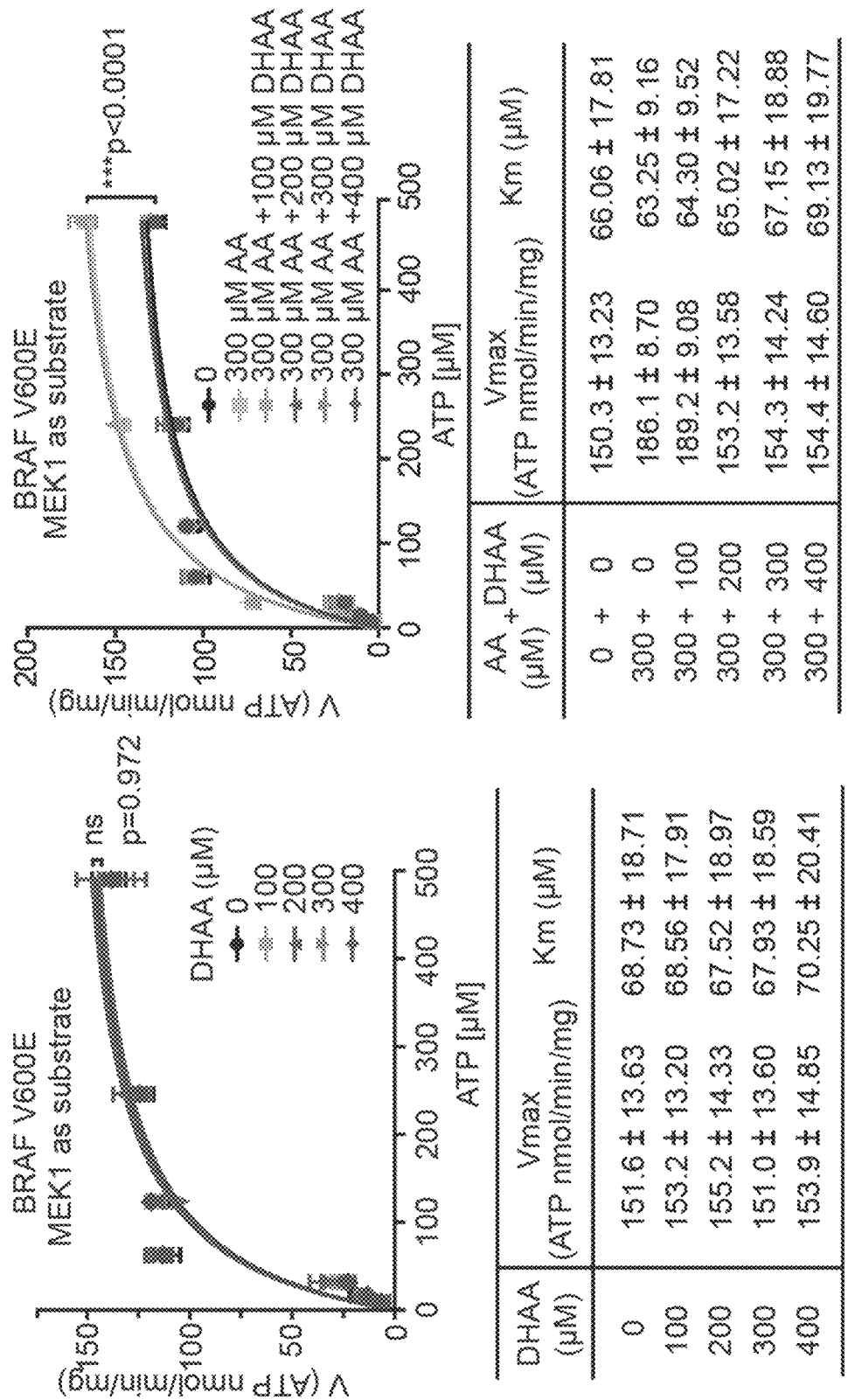
FIG. 4H shows data of Vmax and Km of BRAF V600E measured using purified BRAF V600E protein incubated with increasing concentrations of ATP in the presence and absence of increasing concentration of AA (left panel) or increasing concentration of DHAA with 300 μM AA (right panel), using an excessive amount of purified MEK1 as substrate.
Figure 4I:
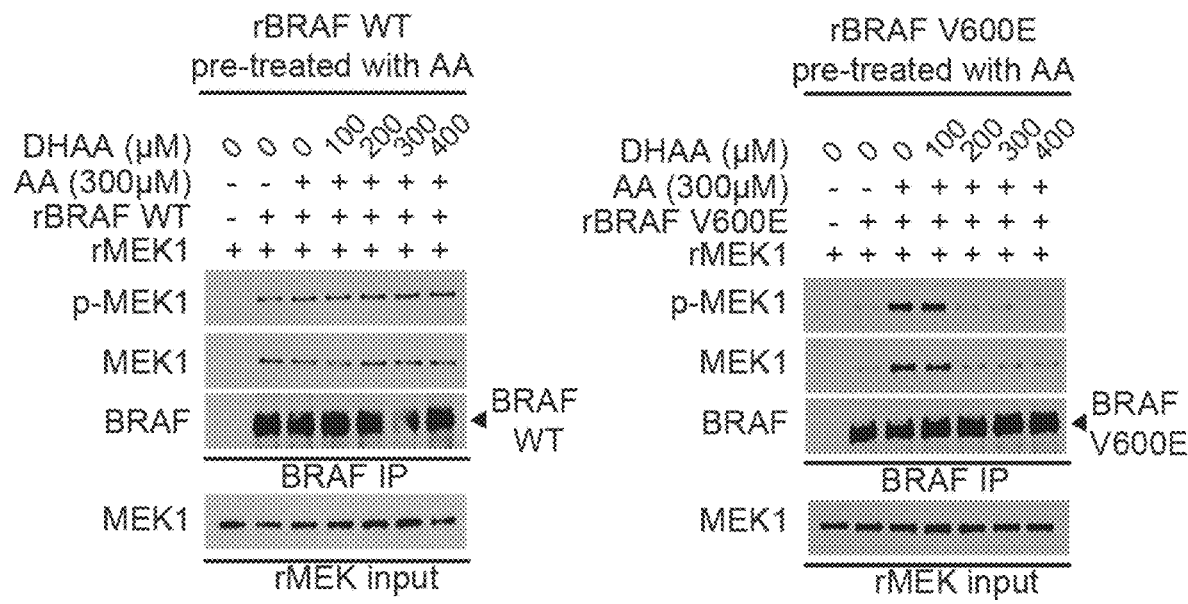
FIG. 4I shows data on the effect of increasing concentrations of DHAA on AA-enhanced rBRAF WT or rBRAF V600E binding to purified recombinant MEK1 (rMEK1).

Whether DHAA inhibits BRAF V600E directly was examined. Acetoacetate binding resulted in increased Vmax and slightly decreased Km of BRAF V600E using MEK1 as a substrate. Interestingly, treatment with increasing concentrations of DHAA alone did not affect BRAF V600E kinase activity with unaltered Vmax and Km (FIG. 4H, left). In contrast, DHAA treatment effectively reversed the activating effect of acetoacetate on BRAF V600E in terms of increased Vmax and decreased Km of BRAF V600E in the presence of acetoacetate (300 µM) when using MEK1 as a substrate (FIG. 4H, right). Further mechanistic studies revealed that DHAA treatment effectively inhibited acetoacetate-enhanced MEK1 binding to BRAF V600E and consequent phosphorylation of V600E-bound MEK1 in a cell-free, in vitro coupled protein-protein binding and kinase assay using purified recombinant BRAF V600E pre-treated with acetoacetate (300 µM) and incubated with recombinant purified MEK1 as a substrate (FIG. 4I right panel). In contrast, DHAA had no effect on BRAF WT-MEK1 binding or MEK1 phosphorylation in a control experiment using purified BRAF WT incubated with MEK1 in the presence of acetoacetate (FIG. 4I left panel). Notably, DHAA at 200 µM was sufficient to compete with acetoacetate at 300 µM for BRAF V600E binding (FIGS. 4E, 4F and 4H) and inhibit BRAF V600E-MEK1 binding and phosphorylation of MEK1 enhanced by acetoacetate at 300 µM (FIG. 4I). This is physiologically consistent with the acetoacetate levels determined as approximately 300 µM in stable HMGCL knockdown A375 and A2058 cells.

Although it is not intended that certain embodiments of this disclosure be limiting by any particular mechanism, these results together are consistent with our hypothesis that mutation at V600 is the predominant mechanism underlying acetoacetate binding to BRAF protein, and DHAA primarily functions by competing with acetoacetate for mutant BRAF binding.

Figure 5A:
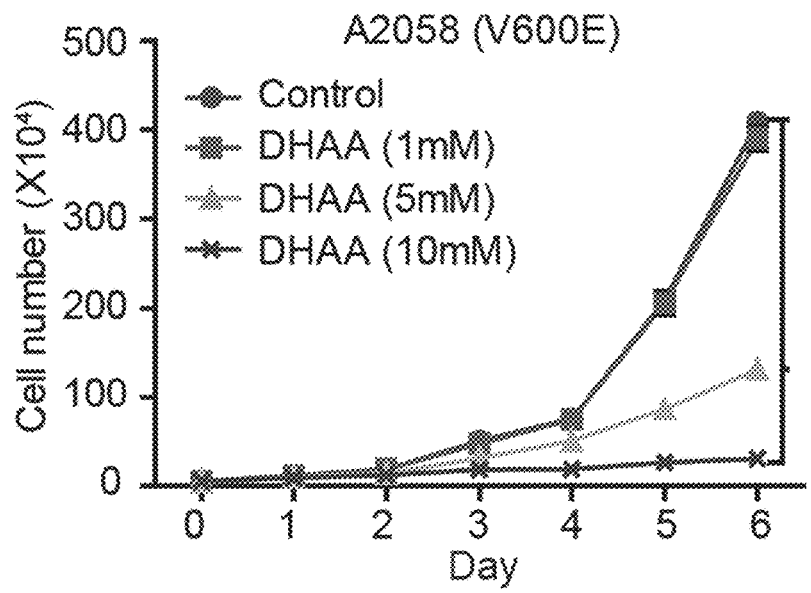
FIG. 5A shows data indicating DHAA selectively inhibits BRAF V600E-positive melanoma cell proliferation effect of DHAA treatment on A2058 cell proliferation.
Figure 5B:
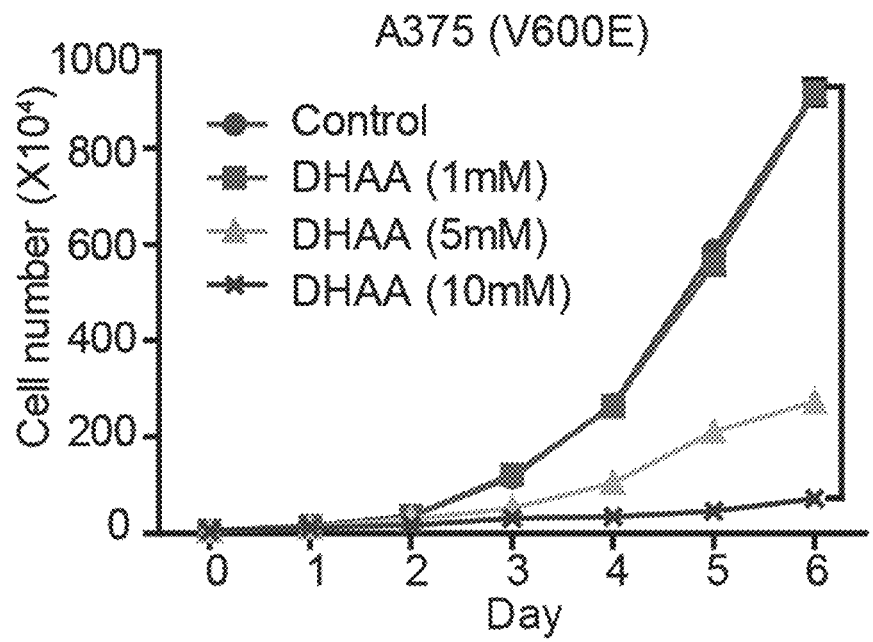
FIG. 5B shows data indicating DHAA selectively inhibits BRAF V600E-positive melanoma cell proliferation effect of DHAA treatment on A375 cell proliferation.
Figure 5C:
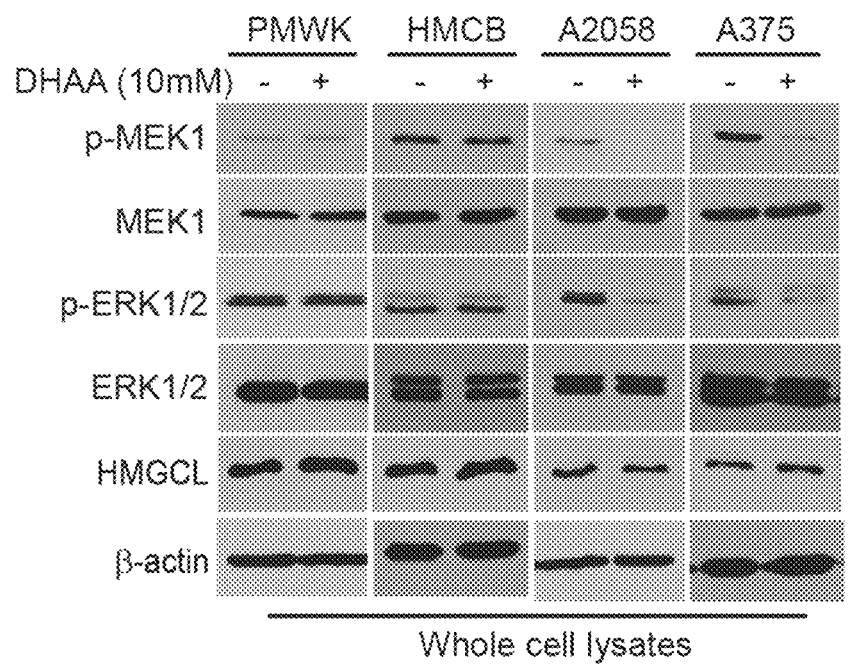
FIG. 5C shows data on MEK1 and ERK1/2 phosphorylation.
Figure 5D:
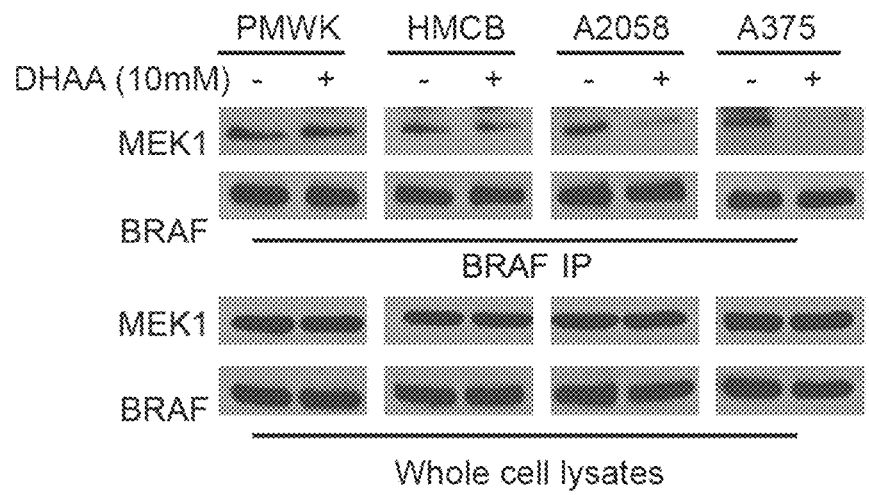
FIG. 5D shows data on BRAF-MEK1 binding.
Figure 5E:
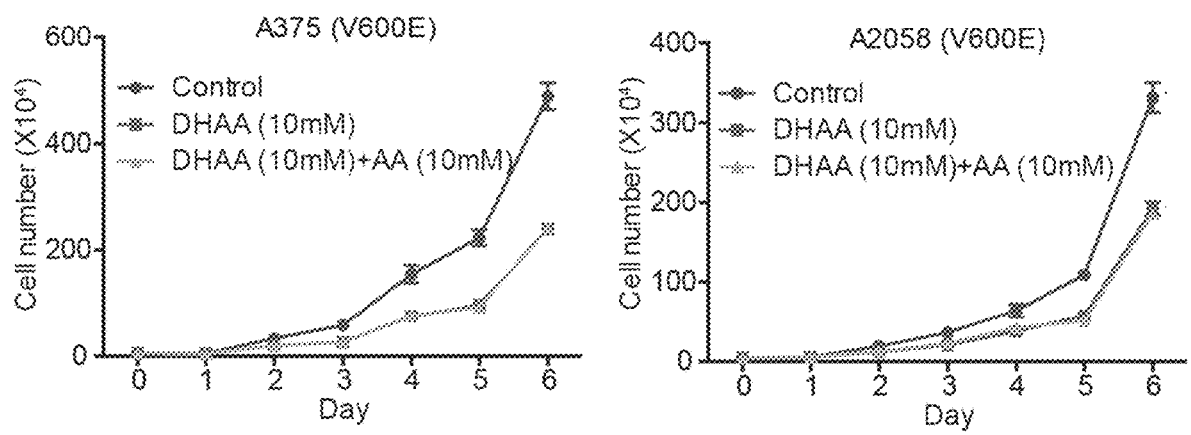
FIG. 5E shows data on the effect of DHAA with or without AA treatment on cell proliferation rates.
Figure 5F:
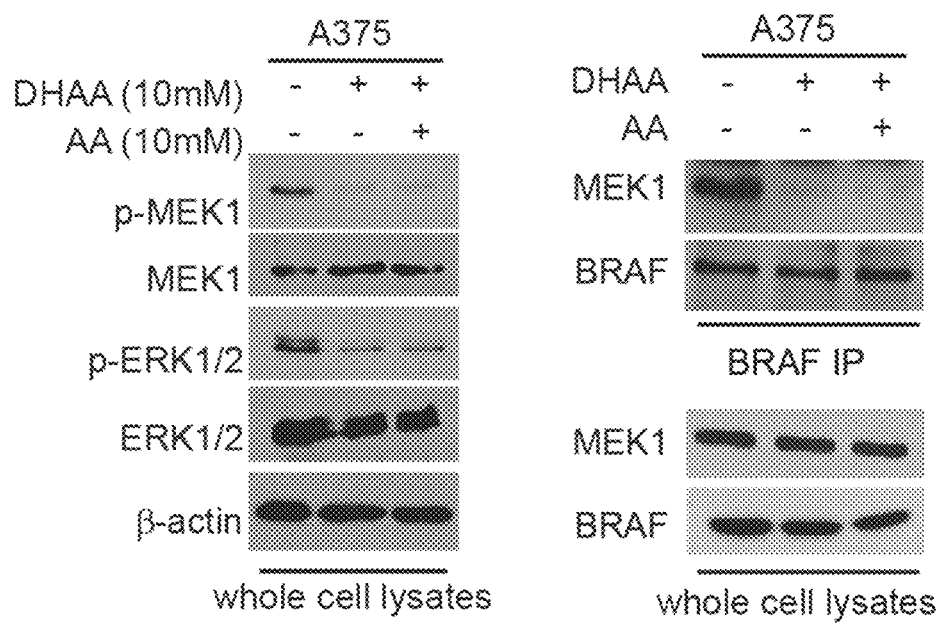
FIG. 5F shows data on MEK1 and ERK1/2 phosphorylation.
Figure 5G:
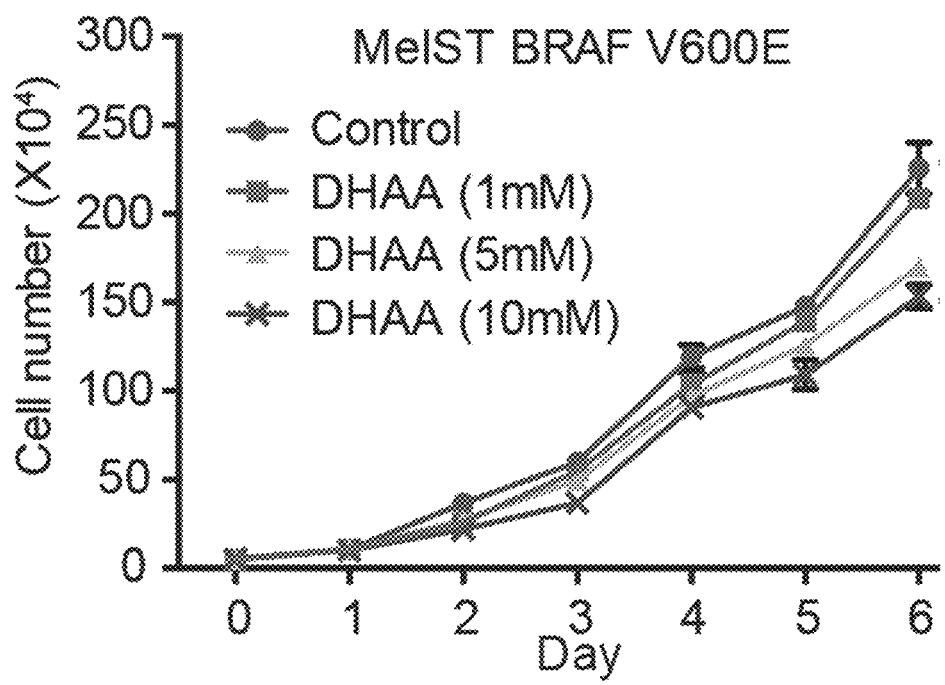
FIG. 5G shows data the effect of DHAA treatment on cell proliferation rates.
Figure 5H:
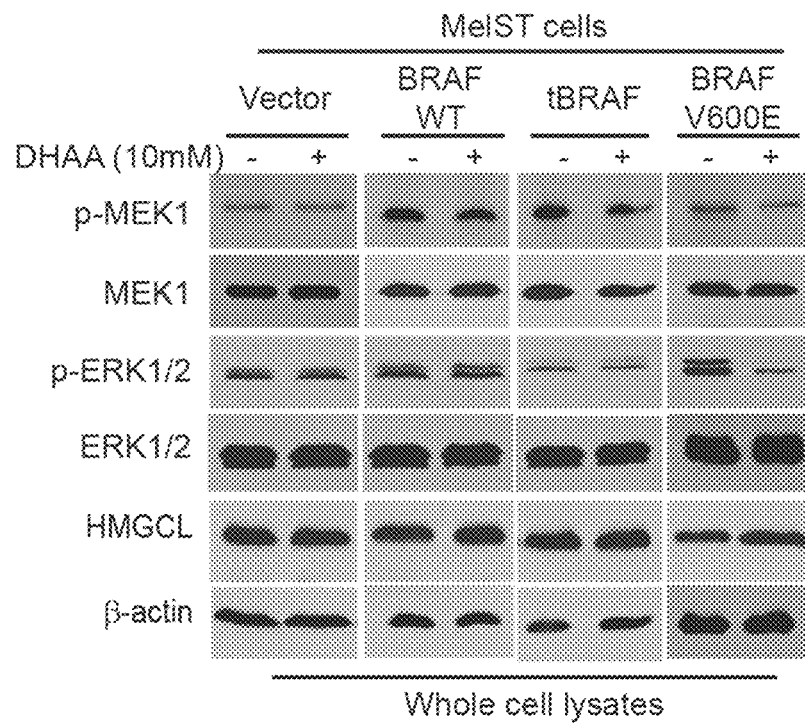
FIG. 5H shows data on MEK1 and ERK1/2 phosphorylation in Me1-ST cells stably expressing BRAF WT, BRAF V600E or a truncated, constitutively active form of BRAF (tBRAF).
Figure 5I:
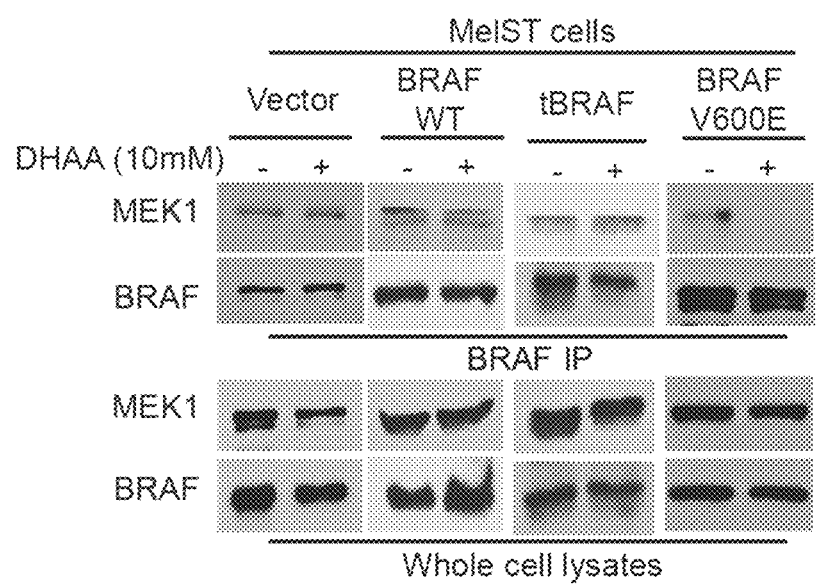
FIG. 5I shows BRAF-MEK1 binding.

DHAA Selectively Inhibits Cell Proliferation and Tumor Growth Potential of BRAF V600E Melanoma Cells DHAA treatment selectively inhibited cell proliferation of A375, A2058 and SK-MEL-5 cells expressing BRAF V600E and WM-266-4 cells expressing BRAF V600D (FIG. 5A), but not control PMWK, CHL-1 and MeWo cells expressing BRAF WT or HMCB and SK-MEL-2 cells expressing active NRAS mutants. Consistent with these findings, DHAA treatment selectively inhibited phosphorylation of MEK1 and ERK1/2 (FIG. 5C) and BRAF V600E-MEK1 association (FIG. 5D) only in BRAF V600E expressing A375 and A2058 cells but not in control PMWK or HMCB cells. The inhibitory effect of DHAA on diverse BRAF V600E-expressing cells could not be reversed by acetoacetate treatment in terms of reduced cell proliferation (FIG. 5E) or decreased MEK-ERK activation (FIG. 5F). Similar results were obtained using immortalized melanocyte Me1-ST cells overexpressing BRAF WT, V600E or tBRAF, where DHAA treatment selectively inhibited cell proliferation, MEK-ERK activation and BRAF V600E-MEK1 binding in BRAF V600E expressing cells but not parental or control cells expressing BRAF WT or tBRAF (FIGS. 5G, 5I, respectively).

Figure 5J:
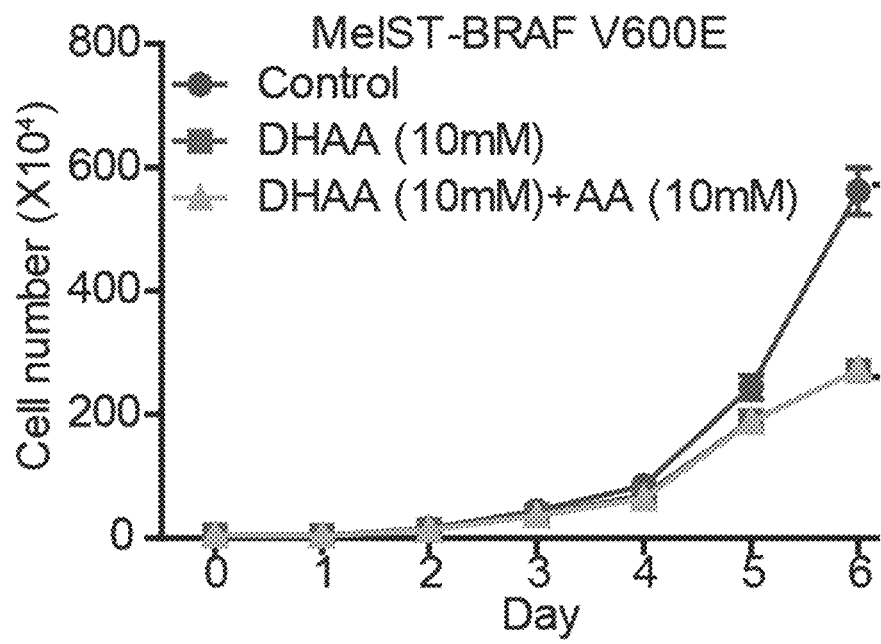
FIG. 5J shows data on the effect of DHAA with or without AA rescue treatment on cell proliferation rates Me1-ST cells stably expressing BRAF V600E.

Acetoacetate treatment did not reverse the inhibitory effect of DHAA on BRAF V600E-expressing Me1-ST cell proliferation (FIG. 5J). Consistent with these findings, DHAA treatment for ~3.5 weeks effectively inhibited xenograft tumor growth rates, sizes and masses in nude mice inoculated subcutaneously with BRAF V600E-expressing human melanoma A2058 and A375 cells but not in mice inoculated with HMCB cells expressing NRAS Q61K. Notably, DHAA treatment did not affect acetoacetate or β-hydroxybutyrate levels in tumors harvested from xenograft mice. In contrast, DHAA treatment selectively inhibited phosphorylation of MEK1 and ERK1/2 without affecting HMGCL expression, reduced binding between BRAF V600E-MEK1, and reduced cell proliferation rates as assessed by IHC staining of Ki67 in tumors derived from A2058 or A375 cells but not control HMCB cells, compared to corresponding control xenograft mice treated with water.

Chronic injection of DHAA to nude mice for ~4 weeks revealed that 200 mg/kg/day administered intraperitoneally is a well-tolerated dose, which did not cause notable differences in histopathological analyses and weights of diverse organs. Moreover, chronic treatment with DHAA had no obvious effect on the mouse gut microbiome, as evidenced by an unaltered total DNA amount extracted from bacteria in mouse feces, suggesting no change in total bacterial number in the mouse gut, and by altered proportions but no loss of any components of the gut microbiota. DHAA treatment did not alter complete blood counts (CBC) or hematopoietic properties in representative A375 xenograft mice compared to the water-treated group. These results together suggest that DHAA treatment does not cause obvious toxicity in vivo.

The inhibitory effect of DHAA treatment on tumor growth potential of A375 cells in xenograft mice was not reversed by intraperitoneal injection with acetoacetate, despite increased serum levels of acetoacetate in DHAA-treated mice receiving acetoacetate injection. DHAA treatment did not affect serum levels of 3HB, cholesterol or glucose in mice in the presence or absence of acetoacetate injection. Consistently, acetoacetate injection did not reverse the inhibitory effects of DHAA on phosphorylation of MEK1 and ERK1/2, BRAF V600E-MEK1 binding or cell proliferation rates assessed by IHC staining of Ki67 in tumors derived from A375 cells in mice. These data are consistent with previous results (FIGS. 5E-5F, 5J) showing that acetoacetate was insufficient to reverse the effect of DHAA on BRAF V600E-expressing cells.

DHAA Reverses Effect of Dietary Fat on BRAF V600E Tumor Growth

Figure 6A:
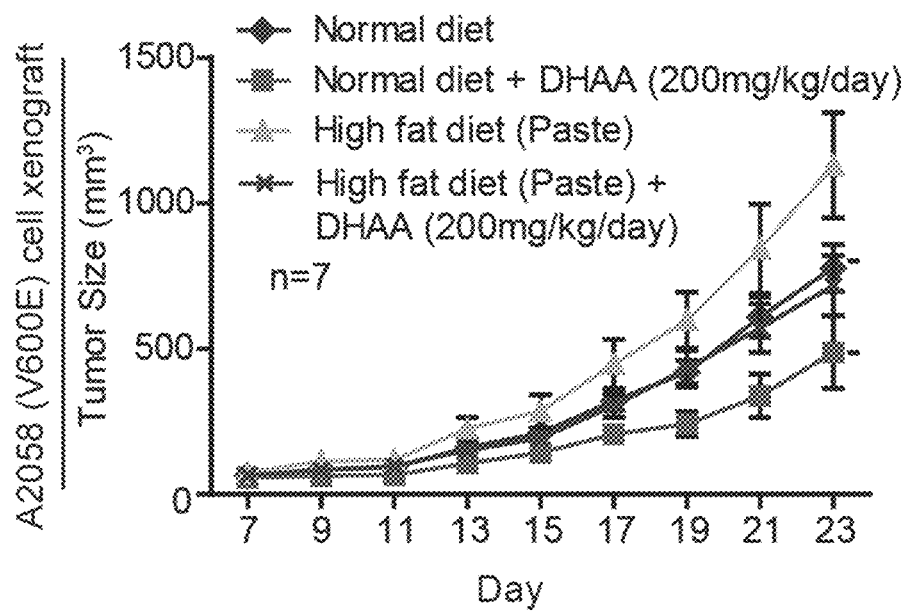
FIG. 6A shows data indicating DHAA treatment reverses high-fat diet-enhanced BRAF V600E tumor growth in xenograft nude mice. Xenograft tumor growth and in nude mice inoculated with BRAF V600E-positive human melanoma A2058 fed with normal or high-fat diets followed by intraperitoneal injection with DHAA.
Figure 6B:
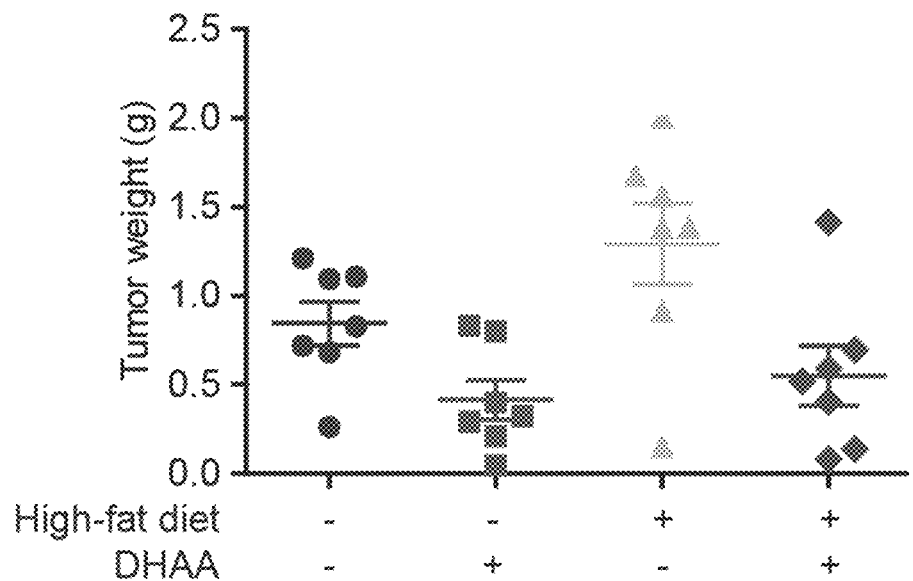
FIG. 6B shows tumor weight for A2058 cells.
Figure 6C:
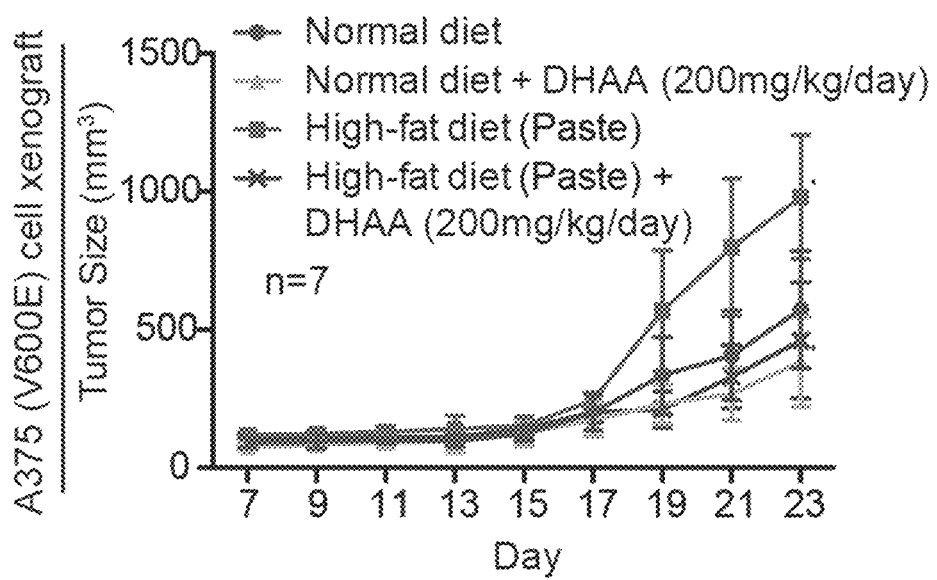
FIG. 6C shows tumor growth in A375 cells.
Figure 6D:
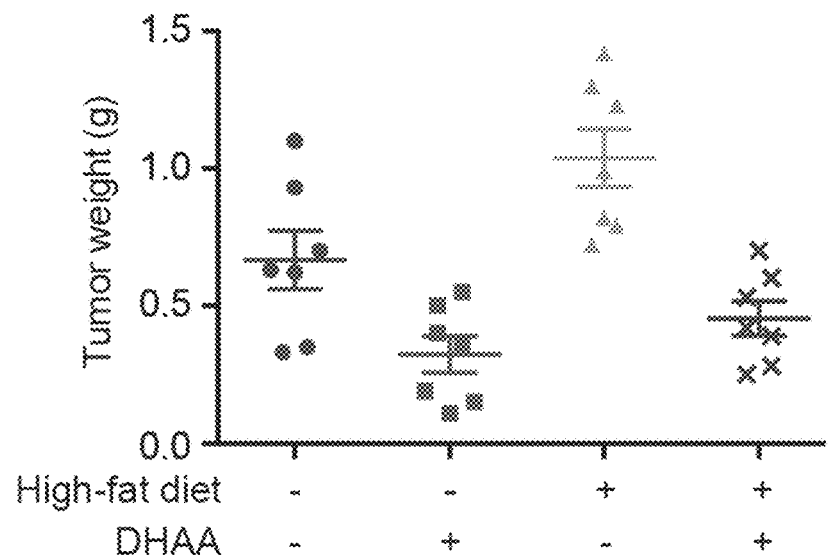
FIG. 6D shows tumor weight for A2058 cells.
Figure 6E:
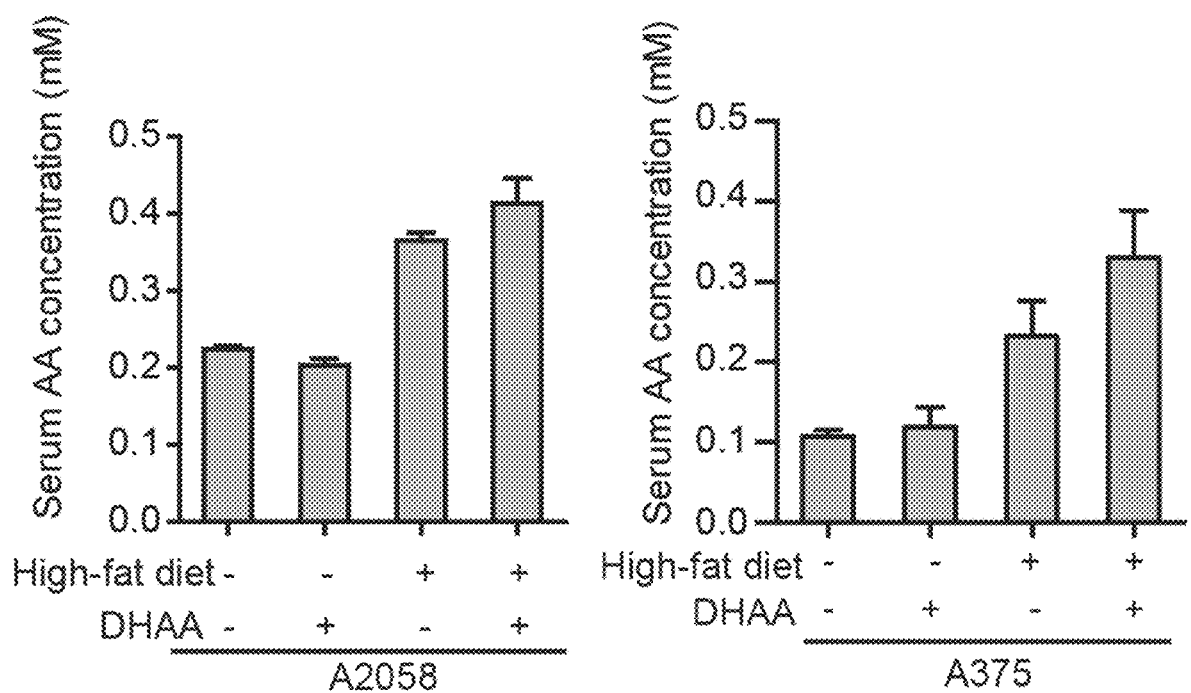
FIG. 6E shows AA (B) levels in serum harvested from xenograft mice.
Figure 6F:
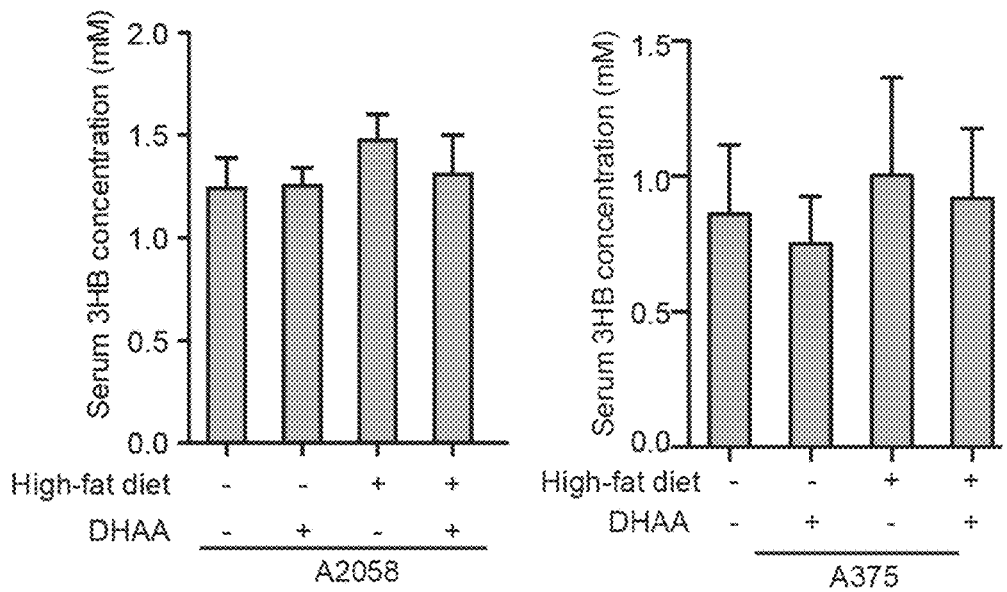
FIG. 6F shows data for 3HB.
Figure 6G:
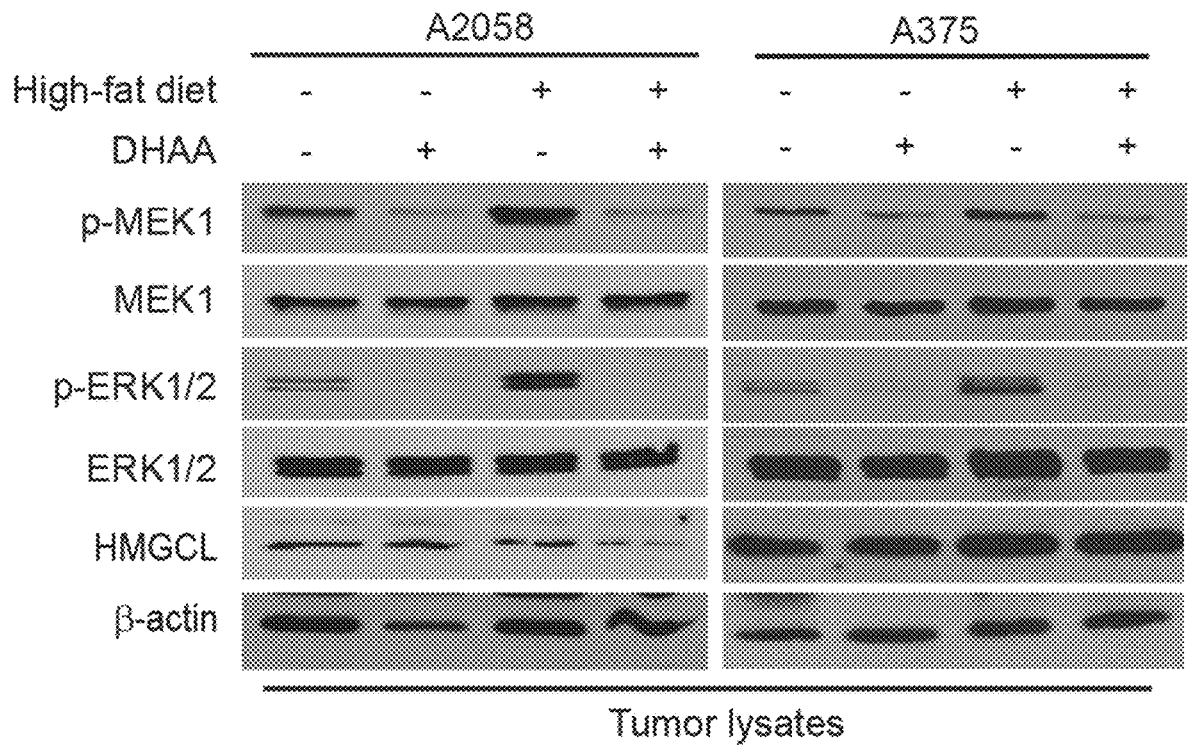
FIG. 6G shows western blot results assessing MEK1 and ERK1/2 phosphorylation.
Figure 6H:
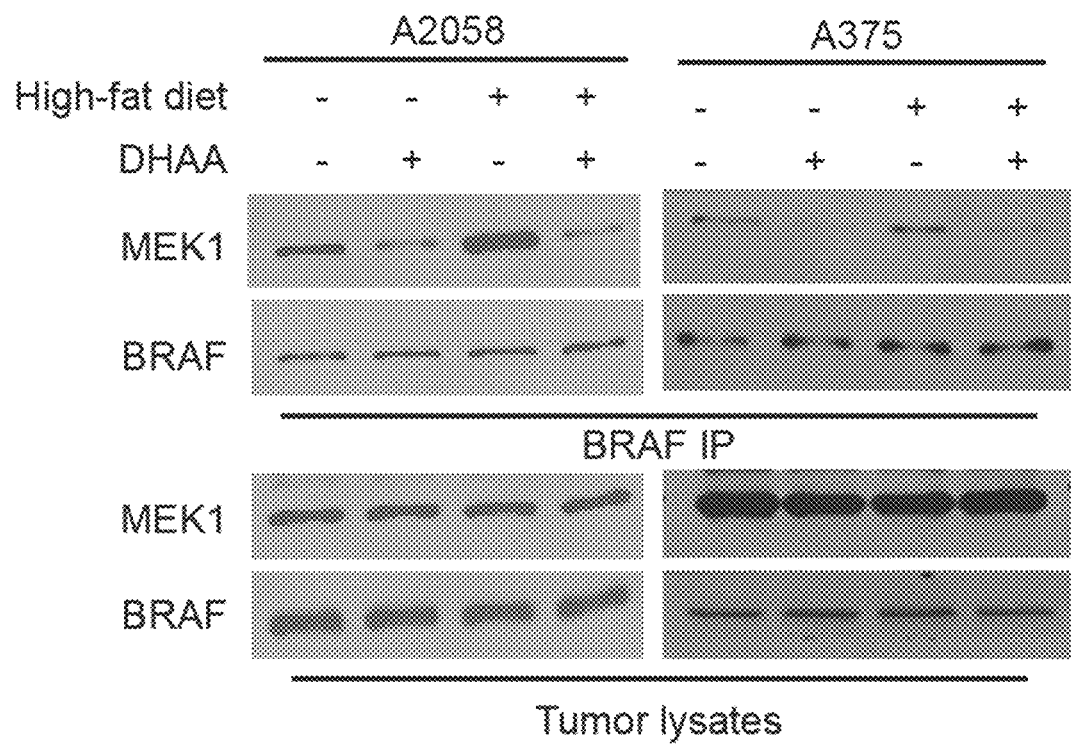
FIG. 6H shows data for BRAF-MEK1 binding in tumor tissue samples obtained from xenograft mice.
Figure 6I:
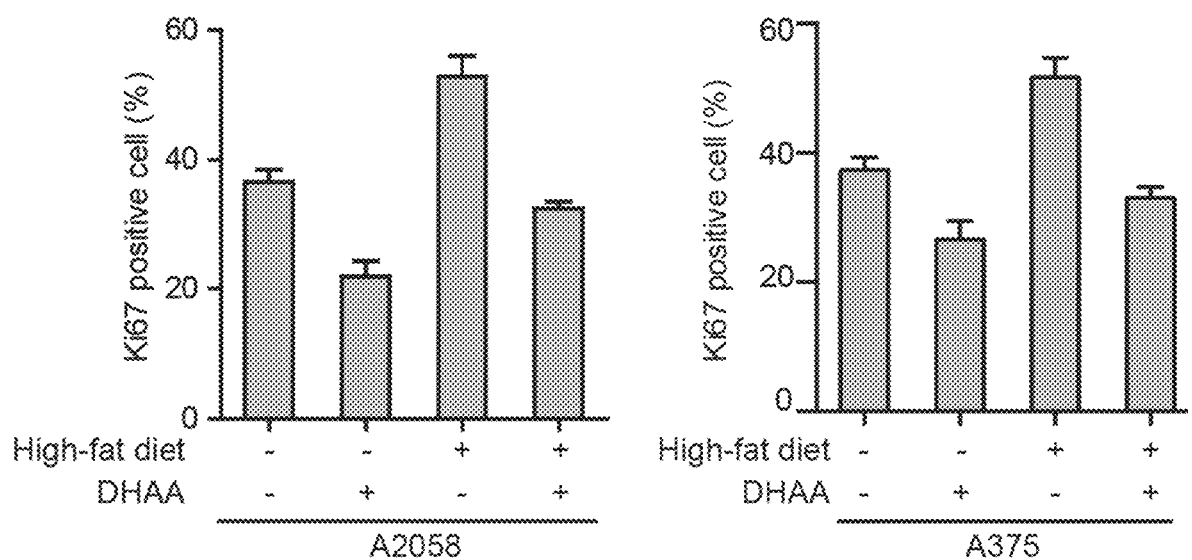
FIG. 6I shows results of IHC staining assay detecting Ki67-positive cells in tumor tissue samples from xenograft mice.

Treatment with a high-fat diet promoted, while DHAA alone inhibited, xenograft tumor growth rates, sizes and masses in nude mice inoculated with BRAF V600E-expressing A2058 or A375 cells, whereas co-treatment with DHAA effectively reversed the enhanced tumor growth potential of A2058 or A375 cells in xenograft mice fed with a high-fat diet (FIG. 6A). A high-fat diet in the presence or absence of DHAA treatment did not affect body weight. Although DHAA treatment had no effect on serum levels of acetoacetate, cholesterol, glucose or 3HB levels in mice fed with high-fat or normal foods (FIGS. 6E-6F), DHAA significantly attenuated the high-fat diet-dependent enhancement of phosphorylation of MEK1 and ERK1/2 (FIG. 6G), BRAF V600E-MEK1 binding (FIG. 6H), and cell proliferation rates assessed by IHC staining of Ki67 (FIG. 6I) in tumors derived from A2058 and A375 cells. These results suggest that dietary fat likely promotes BRAF V600E tumor growth through regulation of serum levels of acetoacetate in vivo.

The invention claimed is:

1. A method of treating cancer or a neoplasm comprising administering an effective amount of dehydroacetic acid, or its derivative, or their salts thereof to a subject in need thereof, wherein the dehydroacetic acid derivative is of the following formula:

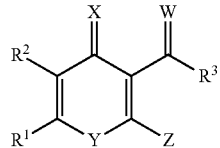

wherein,
W is O;
X is O, S, or NH;
Y is O, S, or NH;
Z is OH, SH, or $NH_2$ optionally substituted with one or more, the same or different $R^{10}$;
$R^1$ is hydrogen, halogen, alkyl, halogenated alkyl, formyl, carboxy, hydroxyalkyl, thioalkyl, aminoalkyl, alkanoyl, alkoxycarbonyl, alkylsulfinyl, alkylsulfonyl, arylsulfonyl, carbocyclyl, benzoyl, benzyl, aryl, or heterocyclyl, wherein $R^1$ is optionally substituted with one or more, the same or different $R^{10}$;
$R^2$ is hydrogen, halogen, alkyl, halogenated alkyl, formyl, carboxy, hydroxyalkyl, thioalkyl, aminoalkyl, alkanoyl, alkoxycarbonyl, alkylsulfinyl, alkylsulfonyl, arylsulfonyl, carbocyclyl, benzoyl, benzyl, aryl, or heterocyclyl, wherein $R^2$ is optionally substituted with one or more, the same or different $R^{10}$;
$R^3$ is hydrogen, alkyl, halogenated alkyl, formyl, carboxy, hydroxyalkyl, thioalkyl, aminoalkyl, alkanoyl, alkoxycarbonyl, alkylsulfinyl, alkylsulfonyl, arylsulfonyl, carbocyclyl, benzoyl, benzyl, aryl, or heterocyclyl, wherein $R^3$ is optionally substituted with one or more, the same or different $R^{10}$; and
$R^{10}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, benzoyl, benzyl, aryl, or heterocyclyl, wherein $R^{10}$ is optionally substituted with one or more, the same or different $R^{11}$; and
$R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydroxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, benzoyl, benzyl, carbocyclyl, aryl, or heterocyclyl.

2. The method of claim 1, wherein the neoplasm has a mutation encoding a V600E amino acid substitution present in the coding sequence for B-Raf.

3. The method of claim 1, wherein the subject is suffering from metastatic melanoma.

4. The method of claim 1, wherein dehydroacetic acid, or its derivative, or their salts thereof is administered in combination with a second therapeutic agent.

* * * * *